(12) United States Patent
Iwata et al.

(10) Patent No.: US 11,365,193 B2
(45) Date of Patent: Jun. 21, 2022

(54) OXADIAZOLE COMPOUND AND FUNGICIDE FOR AGRICULTURAL AND HORTICULTURAL USE

(71) Applicant: Nippon Soda Co., Ltd., Tokyo (JP)

(72) Inventors: Jun Iwata, Odawara (JP); Yuka Nakamura, Odawara (JP); Tsukiho Hayashi, Odawara (JP); Shinya Watanabe, Odawara (JP); Hiroshi Sano, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 255 days.

(21) Appl. No.: 16/625,320

(22) PCT Filed: Jul. 24, 2018

(86) PCT No.: PCT/JP2018/027647
§ 371 (c)(1),
(2) Date: Dec. 20, 2019

(87) PCT Pub. No.: WO2019/022061
PCT Pub. Date: Jan. 31, 2019

(65) Prior Publication Data
US 2021/0403461 A1    Dec. 30, 2021

(30) Foreign Application Priority Data

Jul. 27, 2017 (JP) .............................. JP2017-145283
Aug. 7, 2017 (JP) .............................. JP2017-152642
(Continued)

(51) Int. Cl.
*C07D 413/10* (2006.01)
*A01N 43/82* (2006.01)
(Continued)

(52) U.S. Cl.
CPC ........... *C07D 413/10* (2013.01); *A01N 43/82* (2013.01); *A01N 43/90* (2013.01); *C07D 413/14* (2013.01); *C07D 471/04* (2013.01)

(58) Field of Classification Search
CPC ... C07D 413/10; C07D 413/14; C07D 471/04
See application file for complete search history.

(56) References Cited

U.S. PATENT DOCUMENTS

2010/0261697 A1 * 10/2010 Dorsch .................. A61P 19/02
                                                 514/210.2
2017/0144980 A1    5/2017   Wieja et al.
(Continued)

FOREIGN PATENT DOCUMENTS

| JP | 2010-500297 A | 1/2010 |
|---|---|---|
| WO | WO 2015/185485 A1 | 12/2015 |
| WO | WO 2017/085100 A1 | 5/2017 |
| WO | WO 2017/093019 A1 | 6/2017 |
| WO | WO 2017/093348 A1 | 6/2017 |
| WO | WO 2017/110861 A1 | 6/2017 |
| WO | WO 2017/110862 A1 | 6/2017 |
| WO | WO 2017/118689 A1 | 7/2017 |
| WO | WO-2017/222951 A1 | 12/2017 |
| WO | WO 2018/187553 | * 10/2018 |

(Continued)

OTHER PUBLICATIONS

Print out of specification of U.S. Appl. No. 62/482,343, filed Apr. 6, 2017.*

(Continued)

*Primary Examiner* — Valerie Rodriguez-Garcia
(74) *Attorney, Agent, or Firm* — Foley & Lardner LLP

(57) ABSTRACT

This fungicide for agricultural and horticultural use includes a compound represented by formula (I) (in the formula, X represents a halogen group, or the like; n represents any integer of 0 to 4; when n is 2 or more, X may be the same or different; L represents a single bond or a substituted or unsubstituted C1-6 alkylene group; Q is a group represented by formula (Q-1) or formula (Q-2) (in the formulae, * represents a binding site; $Y^1$ is N or $CR^1$; $Y^2$ is N or $CR^2$; $Y^3$ is N or $CR^3$; $Y^4$ is N or $CR^4$, at least two of $Y^1$ to $Y^4$ are not nitrogen atoms; $R^1$, $R^2$, $R^3$, and $R^4$, each independently represent a hydrogen atom, a substituted or unsubstituted C1-6 alkyl group, or the like; R represents a substituted or unsubstituted C1-6 alkyl group or the like; G represents a substituted or unsubstituted C1-6 alkylene group; T represents a substituted or unsubstituted C1-6 alkylene group; $Y^5$ is N or CH)) or a salt thereof.

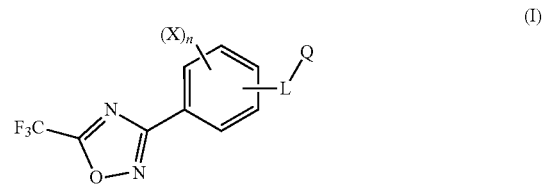

(I)

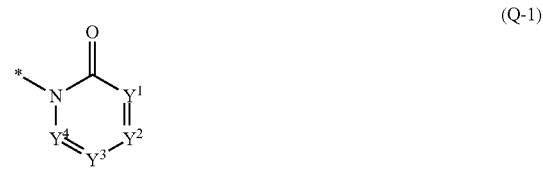

(Q-1)

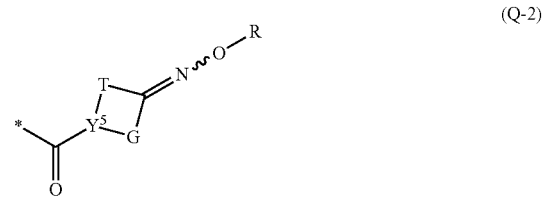

(Q-2)

4 Claims, No Drawings

(30) Foreign Application Priority Data

Nov. 6, 2017 (JP) .............................. JP2017-214071
Apr. 11, 2018 (JP) .............................. JP2018-076406

(51) Int. Cl.
*A01N 43/90* (2006.01)
*C07D 413/14* (2006.01)
*C07D 471/04* (2006.01)

(56) References Cited

U.S. PATENT DOCUMENTS

2020/0148672 A1* 5/2020 Pasteris ................ C07D 417/12
2020/0190076 A1* 6/2020 Hoffman .............. C07D 417/10

OTHER PUBLICATIONS

Supplementary European Search Report dated Dec. 15, 2020 in EP 18838604.9.
International Search Report dated Oct. 16, 2018, in PCT/JP2018/027647.

* cited by examiner

OXADIAZOLE COMPOUND AND FUNGICIDE FOR AGRICULTURAL AND HORTICULTURAL USE

CROSS-REFERENCE TO RELATED APPLICATIONS

This application is the U.S. National Stage of PCT/JP2018/027647, filed Jul. 24, 2018, which claims priority to JP 2017-145283, filed Jul. 27, 2017, JP 2017-152642, filed Aug. 7, 2017, JP 2017-214071, filed Nov. 6, 2017, and JP 2018-076406, filed Apr. 11, 2018.

TECHNICAL FIELD

The present invention relates to an oxadiazole compound and an agricultural or horticultural fungicide. Further particularly, the present invention relates to an oxadiazole compound, that has an excellent fungicidal activity and an excellent safety, and that can be synthesized industrially advantageously, as well as an agricultural or horticultural fungicide containing the same as an active ingradient thereof.

The present invention claims priority on the basis of Japanese Patent Application No. 2017-145283 filed in Japan on Jul. 27, 2017, Japanese Patent Application No. 2017-152642 filed in Japan on Aug. 7, 2017, Japanese Patent Application No. 2017-214071 filed in Japan on Nov. 6, 2017, Japanese Patent Application No. 2018-076406 filed in Japan on Apr. 11, 2018, the contents of which are incorporated herein by reference.

BACKGROUND OF THE INVENTION

In the cultivation of agricultural or horticultural crops, a number of control agents against crop diseases have been proposed. Most proposed control agents are not sufficiently satisfactory in terms of inadequate control efficacy, limited use due to the emergence of drug-resistant pathogens, drug-damaging or causing contamination on plant bodies, toxicity to human or fish or large impact on environment. Therefore, there is a strong need for the emergence of control agents that can be used safely with fewer such disadvantages.

Patent Documents 1 and 2 disclose a compound of formula (A).

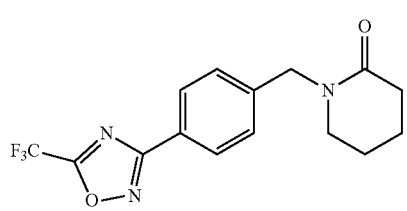

(A)

Patent Document 3 discloses a compound of formula (B).

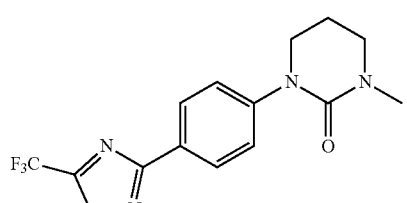

(B)

Patent Document 4 discloses a compound of formula (c).

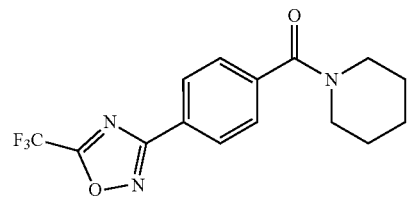

(c)

Patent Document 5 discloses a compound of formula (d).

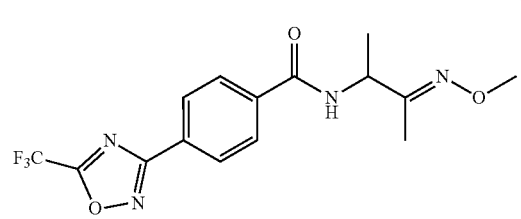

(d)

Patent Document 6 discloses a compound of formula (e).

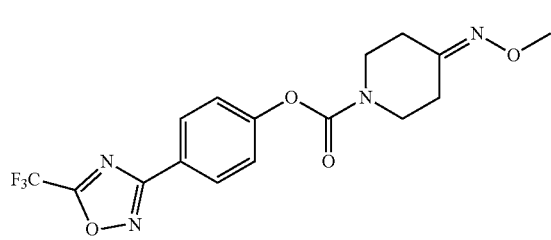

(e)

DOCUMENTS OF RELATED ART

Patent Documents

Patent Document 1: WO 2017/085100 A
Patent Document 2: WO 2017/093348 A
Patent Document 3: WO 2017/110862 A
Patent Document 4: WO 2015/185485 A
Patent Document 5: WO 2017/093019 A
Patent Document 6: WO 2017/110861 A

SUMMARY OF THE INVENTION

Problems to be Solved by the Invention

The present invention aims to provide an oxadiazole compound, that has an excellent fungicidal activity and an excellent safety, and that can be synthesized industrially advantageously, as well as an agricultural or horticultural fungicide containing the same as an active ingredient thereof.

Means to Solve the Problems

The present invention includes the following aspects.
(1) A compound of formula (I) or a salt thereof.

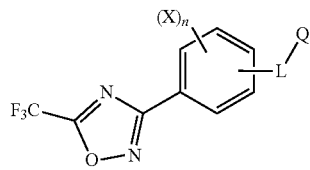

In the formula (I),

X represents a substituted or unsubstituted C1-6 alkyl group, a substituted or unsubstituted C1-6 alkoxy group, or a halogeno group.

n represents a chemically acceptable number of X, and is an integer of 0 to 4. When n is 2 or more, X is identical to or different from each other.

L represents a single bond, or a substituted or unsubstituted C1-6 alkylene group.

Q represents a group of formula (Q-1) or formula (Q-2).

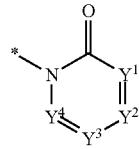

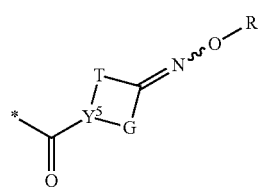

In the formula (Q-1) and formula (Q-2), * represents a bonding position.

In the formula (Q-1), $Y^1$ represents a nitrogen atom or $CR^1$.
$Y^2$ represents a nitrogen atom or $CR^2$.
$Y^3$ represents a nitrogen atom or $CR^3$.
$Y^4$ represents a nitrogen atom or $CR^4$.

However, at least two of $Y^1$ to $Y^4$ do not represent nitrogen atoms.

$R^1$, $R^2$, $R^3$, and $R^4$ each independently represent a hydrogen atom, a substituted or unsubstituted C1-6 alkyl group, a hydroxyl group, a substituted or unsubstituted C1-6 alkoxy group, a substituted or unsubstituted C1-6 alkoxycarbonyl group, a substituted or unsubstituted C1-6 alkylcarbonyloxy group, a substituted or unsubstituted C1-6 alkylthio group, a substituted or unsubstituted alkylsulfinyl group, a substituted or unsubstituted alkylsulfonyl group, a substituted or unsubstituted C6-10 aryl group, a substituted or unsubstituted 5- to 6-membered heterocyclyl group, a substituted or unsubstituted C6-10 aryloxy group, a substituted or unsubstituted amino group, a substituted or unsubstituted aminocarbonyl group, a halogeno group, or a cyano group.

$R^1$ and $R^2$ may be bonded together to form a 5- to 6-membered ring together with two carbon atoms bonding thereto, respectively, or $R^2$ and $R^3$ may be bonded together to form a 5- to 6-membered ring together with two carbon atoms bonding thereto, respectively.

In the formula (Q-2),

R represents a hydrogen atom, a 5- to 6-membered saturated heterocyclyl group or a substituted or unsubstituted C1-6 alkyl group.

G represents a substituted or unsubstituted C1-6 alkylene group.

T represents a substituted or unsubstituted C1-6 alkylene group.

$Y^5$ represents a nitrogen atom or CH.

(2) The compound or the salt thereof according to (1), wherein at least one of $R^1$, $R^2$, $R^3$, and $R^4$ represents a substituted C1-6 alkoxy group, and a substituent on the substituted C1-6 alkoxy group is a halogeno group, a C2-6 alkenyl group, a C1-6 alkoxy group, a C1-6 alkylthio group, a C1-6 alkylsulfinyl group, a C1-6 alkylsulfonyl group, a substituted or unsubstituted C1-6 alkoxyimino group, a 5- to 6-membered saturated heterocyclyloxyimino group, a C6-10 aryloxyimino group, a cyano group or an aminothiocarbonyl group.

(3) The compound or the salt thereof according to (1), wherein the formula (I) is formula (II).

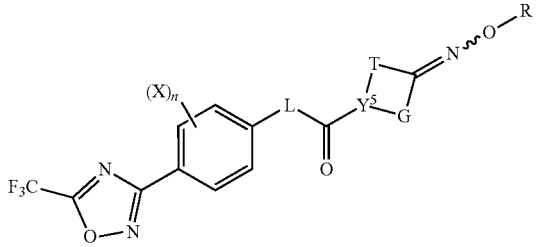

In the formula (II), X, n, and L each represent the same groups as defined in the formula (I), and $Y^1$ to $Y^4$ each represent the same groups as defined in the formula (Q-1).

(4) The compound or the salt thereof according to (1), wherein the formula (I) is formula (III).

(III)

In the formula (III), L represents the same group as defined in the formula (I), and R, G, T and $Y^5$ each represent the same groups as defined in the formula (Q-2).

(5) An agricultural or horticultural fungicide containing at least one selected from the group consisting of a compound and a salt thereof of any one of (1) to (4), as an active ingredient.

Effects of the Invention

An oxadiazole compound according to the present invention has an excellent fungicidal activity and an excellent safety, and can be synthesized industrially advantageously. An agricultural or horticultural fungicide according to the present invention exhibits an excellent control effect without causing harmful effects on plants and provides less toxicity on human, animal, or fish, and less effects on environment.

EMBODIMENTS FOR CARRYING OUT THE INVENTION

Compound of Formula (I)

An oxadiazole compound according to the present invention is a compound of formula (I) (hereinafter, which may be indicated as compound (I)), or a salt of the compound (I).

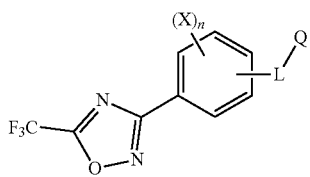

(I)

In the present invention, the term "unsubstituted" refers to a group consisting of a mother nucleus. In the case where only the name of a group serving as a mother nucleus is provided, this refers to "unsubstituted" unless specifically indicated otherwise.

On the other hand, the term "substituted" means that any hydrogen atom of a group serving as a mother nucleus is substituted with a group having a structure that is identical to or different from the mother nucleus. Thus, a "substituent" is another group bound to a group serving as the mother nucleus. The number of substituent may be one or two or more. Two or more substituents may be identical to or different from each other.

The term "C1-6" means that the number of carbon atoms constituting a group serving as a mother nucleus is 1 to 6. The number of carbon atoms does not include the number of carbon atoms constituting a substituent. For example, a butyl group having an ethoxy group as a substituent is classified as a C2 alkoxy C4 alkyl group.

There are no particular limitations on "substituent" provided that the substituent is chemically acceptable and achieves the effects of the present invention. Examples of a group that can be a "substituent" include the following groups:

C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group;

C2-6 alkenyl groups such as a vinyl group, a 1-propenyl group, a 2-propenyl group (an allyl group), a 1-butenyl group, a 2-butenyl group, a 3-butenyl group, a 1-methyl-2-propenyl group, and a 2-methyl-2-propenyl group;

C2-6 alkynyl groups such as an ethynyl group, a 1-propynyl group, a 2-propynyl group, a 1-butynyl group, a 2-butynyl group, a 3-butynyl group, and a 1-methyl-2-propynyl group;

C3-8 cycloalkyl groups such as a cyclopropyl group, a cyclobutyl group, a cyclopentyl group, a cyclohexyl group, and a cubanyl group;

C6-10 aryl groups such as a phenyl group and a naphthyl group;

C6-10 aryl C1-6 alkyl groups such as a benzyl group and a phenetyl group;

3- to 6-membered heterocyclyl groups;

3- to 6-membered heterocyclyl C1-6 alkyl groups;

a hydroxyl group;

C1-6 alkoxy groups such as a methoxy group, an ethoxy group, a n-propoxy group, an i-propoxy group, a n-butoxy group, a s-butoxy group, an i-butoxy group, and a t-butoxy group;

C2-6 alkenyloxy groups such as a vinyloxy group, an allyloxy group, a propenyloxy group, and a butenyloxy group;

C2-6 alkynyloxy groups such as an ethynyloxy group, and a propargyloxy group;

C6-10 aryloxy groups such as a phenoxy group, and a naphthoxy group;

C6-10 aryl C1-6 alkoxy groups such as a benzyloxy group, and a phenetyloxy group;

5- to 6-membered heteroaryloxy groups such as a thiazolyloxy group, and a pyridyloxy group;

5- to 6-membered heteroaryl C1-6 alkyloxy groups such as a thiazolylmethyloxy group, and a pyridylmethyloxy group;

a formyl group;

C1-6 alkylcarbonyl groups such as an acetyl group, and a propionyl group;

a formyloxy group;

C1-6 alkylcarbonyloxy groups such as an acetyloxy group, and a propionyloxy group;

C6-10 arylcarbonyl group such as a benzoyl group;

C1-6 alkoxycarbonyl groups such as a methoxycarbonyl group, an ethoxycarbonyl group, a n-propoxycarbonyl group, an i-propoxycarbonyl group, a n-butoxycarbonyl group, and a t-butoxycarbonyl group;

C1-6 alkoxycarbonyloxy groups such as a methoxycarbonyloxy group, an ethoxycarbonyloxy group, a n-propoxycarbonyloxy group, an i-propoxycarbonyloxy group, a n-butoxycarbonyloxy group, and a t-butoxycarbonyloxy group;

a carboxyl group;

halogeno groups such as a fluoro group, a chloro group, a bromo group, and an iodo group;

C1-6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group;

C2-6 haloalkenyl groups such as a 2-chloro-1-propenyl group, and a 2-fluoro-1-butenyl group;

C2-6 haloalkynyl groups such as a 4,4-dichloro-1-butynyl group, a 4-fluoro-1-pentynyl group, and a 5-bromo-2-pentynyl group;

C1-6 haloalkoxy groups such as a trifluoromethoxy group, a 2-chloro-n-propoxy group, and a 2, 3-dichlorobutoxy group;

C2-6 haloalkenyloxy groups such as a 2-chloropropenyloxy group, and a 3-bromobutenyloxy group;

C1-6 haloalkylcarbonyl groups such as a chloroacetyl group, a trifluoroacetyl group, and a trichloroacetyl group;

an amino group;

C1-6 alkyl-substituted amino groups such as a methylamino group, a dimethylamino group, and a diethylamino group;

C6-10 arylamino groups such as an anilino group, and a naphthylamino group;

C6-10 aryl C1-6 alkylamino groups such as a benzylamino group, and a phenetylamino group;

a formylamino group;

C1-6 alkylcarbonylamino groups such as an acetylamino group, a propanoylamino group, a butyrylamino group, and an i-propylcarbonylamino group;

C1-6 alkoxycarbonylamino groups such as a methoxycarbonylamino group, an ethoxycarbonylamino group, a n-propoxycarbonylamino group, and an i-propoxycarbonylamino group;

unsubstituted or substituted aminocarbonyl groups such as an aminocarbonyl group, a dimethylaminocarbonyl group, a phenylaminocarbonyl group, and a N-phenyl-N-methylaminocarbonyl group;

imino C1-6 alkyl groups such as an iminomethyl group, a (1-imino) ethyl group, and a (1-imino)-n-propyl group;

substituted or unsubstituted N-hydroxyimino-C1-6 alkyl groups such as a N-hydroxy-iminomethyl group, a (1-(N-hydroxy)-imino)ethyl group, a (1-(N-hydroxy)-imino)propyl group, a N-methoxy-iminomethyl group, and a (1-(N-methoxy)-imino)ethyl group;

an aminocarbonyloxy group;

C1-6 alkyl-substituted aminocarbonyloxy groups such as an ethylaminocarbonyloxy group, and a dimethylaminocarbonyloxy group;

a mercapto group;

C1-6 alkylthio groups such as a methylthio group, an ethylthio group, a n-propylthio group, an i-propylthio group, a n-butylthio group, an i-butylthio group, a s-butylthio group, and a t-butylthio group;

C1-6 haloalkylthio groups such as a trifluoromethylthio group, and a 2, 2, 2-trifluoroethylthio group;

C6-10 arylthio groups such as a phenylthio group and a naphthylthio group;

5- to 6-membered heteroarylthio groups such as a thiazolylthio group and a pyridylthio group;

C1-6 alkylsulfinyl groups such as a methylsulfinyl group, an ethylsulfinyl group, and a t-butylsulfinyl group;

C1-6 haloalkylsulfinyl groups such as a trifluoromethylsulfinyl group, and a 2, 2, 2-trifluoroethylsulfinyl group;

C6-10 arylsulfinyl groups such as a phenylsulfinyl group;

5- to 6-membered heteroarylsulfinyl groups such as a thiazolylsulfinyl group, and a pyridylsulfonyl group;

C1-6 alkylsulfonyl groups such as a methylsulfonyl group, an ethylsulfonyl group, and a t-butylsulfonyl group;

C1-6 haloalkylsulfonyl groups such as a trifluoromethylsulfonyl group, and a 2,2,2-trifluoroethylsulfonyl group;

C6-10 arylsulfonyl groups such as a phenylsulfonyl group;

5- to 6-membered heteroarylsulfonyl groups such as a thiazolylsulfonyl group, and a pyridylsulfonyl group;

C1-6 alkylsulfonyloxy groups such as a methylsulfonyloxy group, an ethylsulfonyloxy group, and a t-butylsulfonyloxy group;

C1-6 haloalkylsulfonyloxy groups such as a trifluoromethylsulfonyloxy group, and a 2,2,2-trifluoroethylsulfonyloxy group;

tri-C1-6 alkyl-substituted silyl groups such as a trimethylsilyl group, a triethylsilyl group, and a t-butyldimethylsilyl group;

tri-C6-10 aryl-substituted silyl groups such as a triphenylsilyl group;

a cyano group; and a nitro group.

In addition, any hydrogen atom in the "substituent" may also be substituted with another substituent having a different structure. Examples of such a substituent include C1-6 alkyl groups, C1-6 haloalkyl groups, C1-6 alkoxy groups, C1-6 haloalkoxy groups, halogeno groups, a cyano group, and a nitro group.

The "3- to 6-membered heterocyclyl group" contains 1 to 4 hetero atoms selected from the group consisting of a nitrogen atom, an oxygen atom and a sulfur atom as (a) constituent atom(s) of a ring. The heterocyclyl group may be monocyclic or polycyclic. If at least one ring of the polycyclic heterocyclyl group is a hetero ring, remaining rings thereof may be saturated alicyclic rings, unsaturated alicyclic rings or aromatic rings. Examples of the "3- to 6-membered heterocyclyl group" include 3- to 6-membered saturated heterocyclyl groups, 5- to 6-membered heteroaryl groups, and 5- to 6-membered partially unsaturated heterocyclyl group.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl group include a pyridyl group, a pyrazinyl group, a pyrimidinyl group, a pyridazinyl group, and a triazinyl group.

(X)

In formula (I), X represents a substituted or unsubstituted C1-6 alkyl group, a substituted or unsubstituted C1-6 alkoxy group, or a halogeno group.

The "C1-6 alkyl group" as X may be a straight chain or a branched chain if the carbon number is 3 or more. Examples of the alkyl group include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, a 2,2-dimethylpropyl group, and an i-hexyl group.

The "C1-6 alkoxy group" as X include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Preferable examples of a substituents on the "C1-6 alkyl groups" or the "C1-6 alkoxy group" as X include halogeno groups such as a fluoro group, a chloro group, a bromo group, and an iodo group.

Examples of the "halogeno group" as X include a fluoro group, a chloro group, a bromo group, and an iodo group.

Among these, X preferably represents a halogeno group, and more preferably represents a fluoro group.

(n)

In the formula (I), n is the chemically acceptable number of X, and represents an integer of 0 to 4. In the case where n is 2 or more, a plurality of X is identical to or different from each other.

n is preferably an integer of 0 to 1 and more preferably 0.

(L)

In the formula (I), L represents a single bond or a substituted or unsubstituted C1-6 alkylene group.

Examples of the "C1-6 alkylene group" as L include a methylene group, an ethylene group (a dimethylene group), a trimethylene group, a tetramethylene group, and a propane-1,2-diyl group (that is, a propylene group).

Preferable examples of a substituent on the "C1-6 alkylene groups" as L include: halogeno groups such as a fluoro group, a chloro group, a bromo group, and an iodo group; C1-6 alkyl groups such as a methyl group, an ethyl group, a n-propyl group, a n-butyl group, a n-pentyl group, a n-hexyl group, an i-propyl group, an i-butyl group, a s-butyl group, a t-butyl group, an i-pentyl, a neopentyl group, a 2-methylbutyl group, a 2,2-dimethylpropyl group, and an i-hexyl group; a hydroxy group; C1-6 alkoxy groups such as a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group; C1-6 alkylthio groups such as a methylthio group, an ethylthio group, a n-propylthio group, an i-propylthio group, a n-butylthio group, an i-butylthio group, a s-butylthio group, and a t-butylthio group; an oxo group; a hydroxyimino group; C1-6 alkoxyimino groups such as a methoxyimino group, and an ethoxyimino group; C1-6 haloalkoxyimino groups such as a trifluoromethoxyimino group, and a 2,2,2-trifluoroethoxyimino group; (C1-6 alkylidene amino)oxy group, such as an (ethylidene amino)oxy group and a (propan-2-ylidene amino)oxy group; and C1-6 alkyl group-substituted or unsubstituted 6-oxopyrimidin-1(6H)-yl group, such as a 4-methyl-6-oxopyrimidin-1(6H)-yl group and a 2,4-dimethyl-6-oxopyrimidin-1(6H)-yl group.

Two substituents on the "C1-6 alkylene group" as L may be combined to foil a 5- or 6-membered ring, such as a dioxolane ring or a dioxane ring (preferably a dioxolane ring), together with the respective attached carbon atoms.

Among these, L preferably represents a single bond or a methylene group.

(Q)

In the formula (I), Q is a group of formula (Q-1) or formula (Q-2).

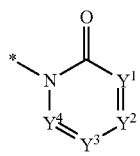
(Q-1)

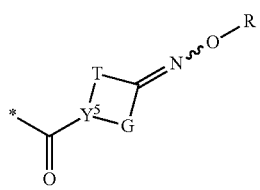
(Q-2)

In the formula (Q-1) and formula (Q-2), * represents a bonding position.

In the formula (Q-1), $Y^1$ represents a nitrogen atom or $CR^1$, $Y^2$ represents a nitrogen atom or $CR^2$, $Y^3$ represents a nitrogen atom or $CR^3$, and $Y^4$ represents a nitrogen atom or $CR^4$. At least two of $Y^1$ to $Y^4$ are not nitrogen atoms.

That is, the group of formula (Q-1) is a group represented by any one of formula (Q-1-1) to formula (Q-1-5).

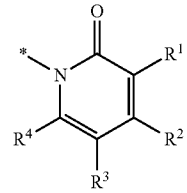
(Q-1-1)

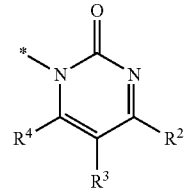
(Q-1-2)

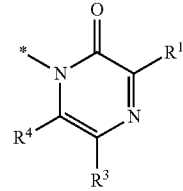
(Q-1-3)

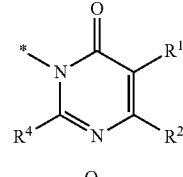
(Q-1-4)

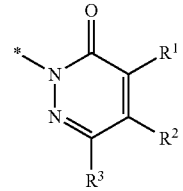
(Q-1-5)

In the formula (Q-1-1) to formula (Q-1-5), * represents the same meaning as that in the formula (Q-1).

The group of formula (Q-1) is preferably a group of formula (Q-1-1), formula (Q-1-4), or formula (Q-1-5).

$R^1$, $R^2$, $R^3$, and $R^4$ each independently represent a hydrogen atom, a substituted or unsubstituted C1-6 alkyl group, a hydroxyl group, a substituted or unsubstituted C1-6 alkoxy group, a substituted or unsubstituted C1-6 alkoxycarbonyl group, a substituted or unsubstituted C1-6 alkylcarbonyloxy group, a substituted or unsubstituted C1-6 alkylthio group, a substituted or unsubstituted alkylsulfonyl group, a substituted or unsubstituted alkylsulfonyl group, a substituted or unsubstituted C6-10 aryl group, a substituted or unsubstituted 5- to 6-membered heteroaryl group, a substituted or unsubstituted amino group, a substituted or unsubstituted aminocarbonyl group, a halogeno group or a cyano group.

Examples of the "C1-6 alkyl group", the "C1-6 alkoxy group", and the "halogeno group", as $R^1$, $R^2$, $R^3$, or $R^4$, include the same groups as those mentioned as X.

Examples of the "C1-6 alkoxycarbonyl group" as $R^1$, $R^2$, $R^3$, or $R^4$, include a methoxycarbonyl group, an ethoxycarbonyl group, a n-propoxycarbonyl group, an i-propoxycarbonyl group, a n-butoxycarbonyl group, and a t-butoxycarbonyl group.

Examples of the "C1-6 alkylcarbonyloxy group" as $R^1$, $R^2$, $R^3$, or $R^4$, include an acetyloxy group and a propionyloxy group.

Examples of the "C1-6 alkylthio group" as $R^1$, $R^2$, $R^3$, or $R^4$, include a methylthio group, an ethylthio group, a n-propylthio group, a n-butylthio group, a n-pentylthio group, a n-hexylthio group, an i-propylthio group, and an i-butylthio group.

Examples of the "C1-6 alkylsulfinyl group" as $R^1$, $R^2$, $R^3$, or $R^4$, include a methylsulfinyl group, an ethylsulfinyl group, and a t-butylsulfinyl group.

Examples of the "C1-6 alkylsulfonyl group" as $R^1$, $R^2$, $R^3$, or $R^4$, include a methylsulfonyl group, an ethylsulfonyl group, and a t-butylsulfonyl group.

Preferable examples of a substituent on the "C1-6 alkyl group", the "C1-6 alkoxycarbonyl group", the "C1-6 alkylcarbonyloxy group", the "C1-6 alkylthio group", the "C1-6 alkylsulfinyl group", or the "C1-6 alkylsulfonyl group", as $R^1$, $R^2$, $R^3$, or $R^4$, include halogeno groups such as a fluoro group, a chloro group, a bromo group, and an iodo group.

Preferable examples of a substituent on the "C1-6 alkoxy group", as $R^1$, $R^2$, $R^3$, or $R^4$, include halogeno groups, C2-6 alkenyl groups, C1-6 alkoxy groups, C1-6 alkylthio groups, C1-6 alkylsulfinyl groups, C1-6 alkylsulfonyl groups, substituted or unsubstituted C1-6 alkoxyimino groups (preferably, C1-6 alkoxyimino groups which may have, as a substituent, a C1-6 alkoxy group, a C6-10 aryl group (preferably a phenyl group), a halogeno group, or a cyano group), 5- to 6-membered saturated heterocyclyloxyimino groups (preferably a tetrahydropyranyloxyimino group), C6-10 aryloxyimino groups (preferably a phenoxyimino group), a cyano group and an aminothiocarbonyl group.

Specific examples thereof include: halogeno groups such as a fluoro group, a chloro group, a bromo group, and an iodo group; C2-6 alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 alkylthio groups such as a methylthio group, an ethylthio group, a n-propylthio group, an i-propylthio group, a n-butylthio group, an i-butylthio group, a s-butylthio group, and a t-butylthio group; C1-6 alkylsulfinyl groups such as a methylsulfinyl group, an ethylsulfinyl group, and a t-butylsulfinyl group; C1-6 alkylsulfonyl groups such as a methylsulfonyl group, an ethylsulfonyl group, and a t-butylsulfonyl group; substituted or unsubstituted C1-6 alkoxyimino groups such as a methoxyimino group, an ethoxyimino group, a 2-methoxyethoxyimino group, a 2,2-difluoroethoxyimino group, a benzyloxyimino group, and a cyanomethoxyimino group; 5- to 6-membered saturated heterocyclyloxyimino groups such as a (tetrahydro-2H-pyran-2-yl)oxyimino group; C6-10 aryloxyimino groups such as a phenoxyimino group; a cyano group; and an aminothiocarbonyl group.

Examples of the "C6-10 aryl group" as R', $R^2$, $R^3$, or $R^4$, include a phenyl group, and a naphthyl group. Among these, a phenyl group is preferable.

The "5- to 6-membered heterocyclyl group" as $R^1$, $R^2$, $R^3$, or $R^4$ contains 1 to 4 hetero atoms selected from the group consisting of a nitrogen atom, an oxygen atom and a sulfur atom, as (a) constituent atom(s) of the ring. Examples of the "5- to 6-membered heterocyclyl group" include 5- to 6-membered saturated heterocyclyl groups, 5- to 6-membered heteroaryl groups, and 5- to 6-membered partially unsaturated heterocyclyl groups.

Examples of the 5- to 6-membered saturated heterocyclyl group include a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered heteroaryl group include a pyridyl group, a pyrazinyl group, a pyrimidinyl group, a pyridazinyl group, and a triazinyl group.

Among these, a triazolyl group, an oxadiazolyl group, or a morpholinyl group is preferable.

Examples of the "C6-10 aryloxy group" as R', $R^2$, $R^3$, or $R^4$, include a phenoxy group and a naphthyloxy group. Among these, a phenoxy group is preferable.

Preferable examples of a substituent on the "C6-10 aryl group" or the "5- to 6-membered heteroaryl group", as $R^1$, $R^2$, $R^3$, or $R^4$, include: halogeno groups such as a fluoro group, a chloro group, a bromo group, and an iodo group; and C1-6 haloalkyl groups such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group, and a 2,4,6-trichlorohexyl group.

The "substituted or unsubstituted amino group" as $R^1$, $R^2$, $R^3$, or $R^4$ is a group represented by "—$NR^a R^b$". In the formula, $R^a$ and $R^b$ each independently represent a hydrogen atom, a benzyl group, a formyl group, a substituted or unsubstituted C1-6 alkylcarbonyl group, a benzoyl group, a C1-6 alkoxycarbonyl group or a phenyl group.

Examples of the "C1-6 alkoxycarbonyl group" as $R^a$ or $R^b$ include the same groups as mentioned as R', $R^2$, $R^3$, or $R^4$.

Examples of the "C1-6 alkylcarbonyl group" as $R^a$ or $R^b$ include an acetyl group, and a propionyl group.

Preferable examples of a substituent on the "C1-6 alkylcarbonyl group", as $R^a$ or $R^b$, include: halogeno groups such as a fluoro group, a chloro group, a bromo group, and an iodo group; and C1-6 alkoxy groups such as a methoxy group, an ethoxy group, a n-propoxy group, an i-propoxy group, a n-butoxy group, a s-butoxy group, an i-butoxy group, and a t-butoxy group.

It is preferable that $R^1$, $R^2$, $R^3$, and $R^4$ each independently represent a hydrogen atom, a substituted or unsubstituted C1-6 alkyl group, a hydroxyl group, a substituted or unsubstituted C1-6 alkoxy group or a substituted or unsubstituted amino group.

In the formula (Q-1), $R^1$ and $R^2$ may be combined to form a 5- or -6 membered ring with two carbon atoms to which $R^1$ and $R^2$ are bonded, respectively.

In the case where $R^1$ and $R^2$ are combined to form a 5- or -6 membered ring with two carbon atoms to which $R^1$ and $R^2$ are bonded, respectively, examples of the group of the formula (Q-1) include groups of formula (Q-1-6) to formula (Q-1-12).

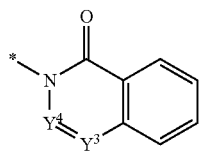
(Q-1-6)

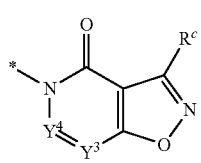
(Q-1-7)

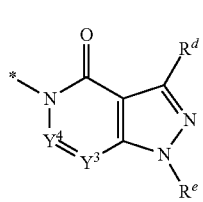
(Q-1-8)

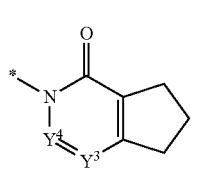
(Q-1-9)

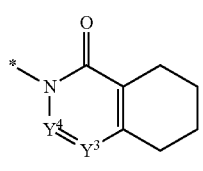
(Q-1-10)

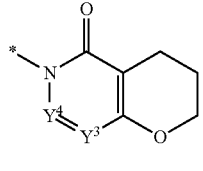
(Q-1-11)

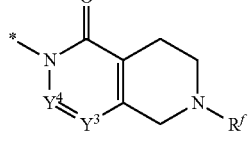
(Q-1-12)

In the formula (Q-1-6) to formula (Q-1-12), *, $Y^3$ and $Y^4$ are the same groups as those defined in the formula (Q-1).

In the formula (Q-1-7), $R^c$ represents a hydrogen atom or a C1-6 alkyl group.

Examples of the "C1-6 alkyl group" as $R^c$ include the same groups as those mentioned as X mentioned above.

In the formula (Q-1-8), $R^d$ and $R^e$, each independently represent, a hydrogen atom or a C1-6 alkyl group.

Examples of the "C1-6 alkyl group" as $R^d$ and $R^e$ include the same groups as those mentioned as X.

In the formula (Q-1-12), $R^f$ represents a hydrogen atom, a substituted or unsubstituted C1-6 alkylcarbonyl group, a benzoyl group, or a C1-6 alkoxycarbonyl group.

Examples of the "C1-6 alkylcarbonyl group" as $R^f$ include the same groups as those mentioned as $R^a$ and $R^b$.

Preferable examples of a substituent on the "C1-6 alkylcarbonyl group" as $R^f$ include C1-6 alkoxy groups such as a methoxy group, an ethoxy group, a n-propoxy group, an i-propoxy group, a n-butoxy group, a s-butoxy group, an i-butoxy group, and a t-butoxy group.

Examples of the "C1-6 alkoxycarbonyl group" as $R^f$ include the same groups as those mentioned as $R^1$, $R^2$, $R^3$, or $R^4$.

In the formula (Q-1), $R^2$ and $R^3$ may be combined to form a 5- to 6-membered ring with two carbon atoms to which $R^2$ and $R^3$ are bonded, respectively.

When $R^2$ and $R^3$ are combined to form a 5- to 6-membered ring with the two carbon atoms to which $R^2$ and $R^3$ are each bonded, examples of the group of the formula (Q-1) include groups of formulae (Q-1-13) and (Q-1-14).

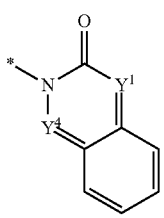
(Q-1-13)

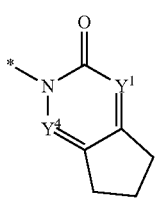
(Q-1-14)

In the formulae (Q-1-13) and (Q-1-14), *, $Y^1$ and $Y^4$ represent the same groups as those in the formula (Q-1).

In the formula (Q-2), R represents a hydrogen atom, a 5- to 6-membered saturated heterocyclyl group or a substituted or unsubstituted C1-6 alkyl group.

Examples of the "5- to 6-membered saturated heterocyclyl group" as R include a pyrrolidinyl group, a tetrahydrofuranyl group, a thiazolidinyl group, a piperidyl group, a piperazinyl group, a morpholinyl group, a dioxolanyl group, a dioxanyl group, and a tetrahydropyranyl group, and the 5- to 6-membered saturated heterocyclyl group is preferably a tetrahydropyranyl group.

Examples of the "C1-6 alkyl group" as R include the same groups as those mentioned as X.

Preferable examples of a substituent on the "C1-6 alkyl group" as R include: halogeno groups such as a fluoro group, a chloro group, a bromo group, and an iodo group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 alkylthio groups such as a methylthio group, an ethylthio group, a n-propylthio group, a n-butylthio group, a n-pentylthio group, a n-hexylthio group, an i-propylthio group, and an i-butylthio group; C1-6 alkylsulfinyl groups such as a methylsulfinyl group, an ethylsulfinyl group, and a t-butylsulfinyl group; C1-6 alkylsulfonyl groups such as a methylsulfonyl group, an ethylsulfonyl group, and a t-butylsulfonyl group; C3-8 cycloalkyl groups such as a cyclopropyl group, a cyclobutyl group, a cyclopentyl group, a cyclohexyl group, a cycloheptyl group, and a cubanyl group; a phenyl group; and a cyano group, and more preferable examples thereof include halogeno groups, C1-6 alkoxy groups, C1-6 alkylsulfinyl groups, C3-8 cycloalkyl groups, and a cyano group.

R preferably represents a substituted or unsubstituted C1-6 alkyl group, and more preferably represents a C1-6 alkyl group.

In the formula (Q-2), G and T each represent a substituted or unsubstituted C1-6 alkylene group.

Examples of the "C1-6 alkylene group" as G and T include the same groups as those mentioned as L.

Preferable examples of a substituent on the "C1-6 alkylene group" as G or T include: C1-6 alkyl groups such as a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, a 2,2-dimethylpropyl group, and an i-hexyl group; C1-6 alkylthio groups such as a methylthio group, an ethylthio group, a n-propylthio group, a n-butylthio group, a n-pentylthio group, a n-hexylthio group, an i-propylthio group, and an i-butylthio group; C1-6 alkylsulfinyl groups such as a methylsulfinyl group, an ethylsulfinyl group, and a t-butylsulfinyl group; and C1-6 alkylsulfonyl groups such as a methylsulfonyl group, an ethylsulfonyl group, and a t-butylsulfonyl group. Among these, a C1-6 alkyl group is preferable.

G and T each preferably represent a C1-6 alkylene group, and more preferably represent a methylene group or an ethylene group.

A wave line representing the bond between nitrogen and oxygen in the formula (Q-2) (N—O undefined stero bond) indicates the presence of the E or Z body or mixtures thereof due to the nitrogen carbon double bond.

In the formula (Q-2), $Y^5$ represents a nitrogen atom or CH, and preferably represents a nitrogen atom.

Salts of the compound (I) are not particularly limited in the case of agriculturally or horticulturally acceptable salts. Examples thereof include salts of inorganic acids such as a hydrochloric acid or a sulfuric acid; salts of organic acids such as an acetic acid or a lactic acid; salts of alkali metals such as lithium, sodium or potassium; salts of alkaline earth metals such as calcium or magnesium; salts of transition metals such as iron or copper; and salts of organic bases such as ammonia, triethylamine, tributylamine, pyridine, or hydrazine.

The compound (I) or the salts of the compound (I) are not particularly limited by the preparation process thereof. The salts of the compound (I) may be obtained from the compound (I) by known methods. For example, a compound (I) or a salt of the compound (I) according to the present invention may be obtained by the process described in Examples, or the like.

Compound of Formula (II)

An oxadiazole compound according to the present invention is preferably a compound of formula (II).

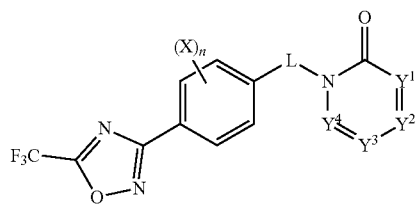

(II)

In the formula (II), X, n and L represent the same groups as those in the formula (I), and $Y^1$ to $Y^4$ represent the same groups as those in the formula (Q-1).

Compound of Formula (IV)

An oxadiazole compound according to the present invention is preferably a compound of formula (IV).

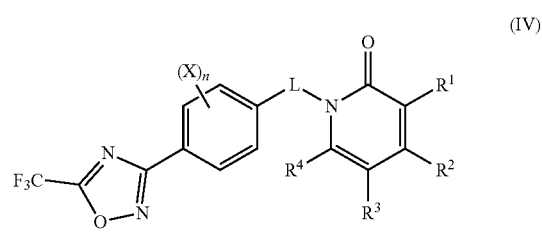

(IV)

In the formula (IV), X, n and L represent the same groups as those in the formula (I), and $R^1$ to $R^4$ represent the same groups as mentioned above.

Compound of Formula (V)

An oxadiazole compound according to the present invention is preferably a compound of formula (V).

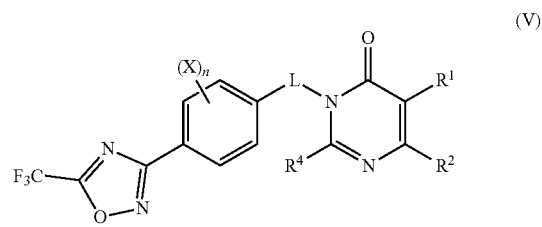

(V)

In the formula (V), X, n and L represent the same groups as those in the formula (I), and $R^1$, $R^2$ and $R^4$ represent the same groups as mentioned above.

Compound of Formula (VI)

An oxadiazole compound according to the present invention is preferably a compound of formula (VI).

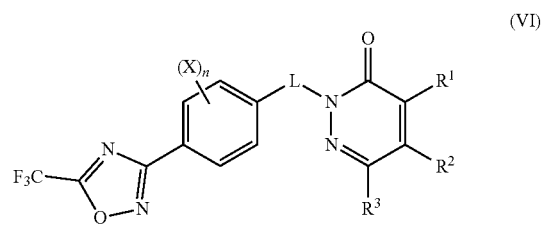

(VI)

In the formula (VI), X, n and L represent the same groups as those in the formula (I), and $R^1$ to $R^3$ represent the same groups as mentioned above.

Compound of Formula (III)

An oxadiazole compound according to the present invention is preferably a compound of formula (III).

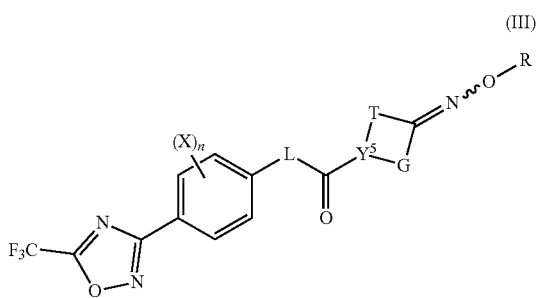

(III)

In the formula (III), L represent the same group as defined in the formula (I), and R, T, G and $Y^5$ represent the same groups as those in the formula (Q-2).

A wave line representing the bond between nitrogen and oxygen in the formula (III) (N—O undefined stero bond) indicates the presence of the E or Z body or mixtures thereof due to the nitrogen carbon double bond.

In the formula (III), L preferably represents a single bond or a methylene group, R preferably represents a C1-6 alkyl group or a C1-6 haloalkyl group, T preferably represents a methylene group or an ethylene group, and G preferably represents a methylene group or an ethylene group.

(Agricultural or Horticultural Fungicide)

An agricultural or horticultural fungicide according to the present invention contains at least one selected from the group consisting of a compound (I) and salts thereof, as an active ingradient. The amount of the compound (I) or the salts thereof contained in the agricultural or horticultural fungicide according to the present invention is not particularly limited provided that the amount allows fungicidal effects to be exhibited.

The agricultural or horticultural fungicide according to the present invention may be used to control plant disease caused by a wide variety of fungi, such as Oomycetes, Ascomycetes, Deuteromycetes, Basidiomycetes, or Zygomycetes.

Examples of plant diseases (pathogens) to be controlled are shown below.

Sugar beet: brown spot disease (*Cercospora beticola*), black root disease (*Aphanomyces cochlioides*), root rot disease (*Thanatephorus cucumeris*), leaf rot disease (*Thanatephorus cucumeris*), and the like.

Peanut: brown spot disease (*Mycosphaerella arachidis*), leaf mold (*Ascochyta* sp.), rust disease (*Puccinia arachidis*), damping-off disease (*Pythium debaryanum*), rust spot disease (*Alternaria alternata*), stem rot disease (*Sclerotium rolfsii*), black rust disease (*Mycosphaerella berkeleyi*), and the like.

Cucumber: powdery mildew (*Sphaerotheca fuliginea*), downy mildew (*Pseudoperonospora cubensis*), gummy stem blight (*Mycosphaerella melonis*), wilt disease (*Fusarium oxysporum*), sclerotinia rot (*Sclerotinia sclerotiorum*), gray mold (*Botrytis cinerea*), anthracnose (*Colletotrichum orbiculare*), scab (*Cladosporium cucumerinum*), brown spot disease (*Corynespora cassiicola*), damping-off disease (*Pythium debaryanum, Rhizoctonia solani* Kuhn), *Phomopsis* root rot disease (*Phomopsis* sp.), Bacterial spot (*Pseudomonas syringae* pv. *Lechrymans*), and the like.

Tomato: gray mold disease (*Botrytis cinerea*), leaf mold disease (*Cladosporium fulvum*), late blight disease (*Phytophthora infestans*), Verticillium wilt disease (*Verticillium albo-atrum, Verticillium dahliae*), powdery mildew disease (*Oidium neolycopersici*), early blight disease (*Alternaria solani*), leaf mold disease (*Pseudocercospora fuligena*), and the like.

Eggplant: gray mold disease (*Botrytis cinerea*), black rot disease (*Corynespora melongenae*), powdery mildew disease (*Erysiphe cichoracearum*), leaf mold disease (*Mycovellosiella nattrassii*), sclerotinia rot disease (*Sclerotinia sclerotiorum*), Verticillium wilt disease (*Verticillium dahlia*), *Mycosphaerella* blight (*Phomopsis vexans*), and the like.

Strawberry: gray mold disease (*Botrytis cinerea*), powdery mildew disease (*Sphaerotheca humuli*), anthracnose disease (*Colletotrichum acutatum, Colletotrichum fragariae*), phytophthora rot disease (*Phytophthora cactorum*), soft rot disease (*Rhizopus stolonifer*), fsarium wilt disease (*Fusarium oxysporum*), verticillium wilt disease (*Verticillium dahlia*), and the like.

Onion: neck rot disease (*Botrytis allii*), gray mold disease (*Botrytis cinerea*), leaf blight disease (*Botrytis squamosa*), downy mildew disease (*Peronospora destructor*), Phytophthora porn disease (*Phytophthora porn*), and the like.

Cabbage: clubroot disease (*Plasmodiophora brassicae*), soft rot disease (*Erwinia carotovora*), black rot disease (*Xanthomonas campesrtis* pv. *campestris*), bacterial black spot disease (*Pseudomonas syringae* pv. *Maculicola*, P.s. pv. *alisalensis*), downy mildew disease (*Peronospora parasitica*), sclerotinia rot disease (*Sclerotinia sclerotiorum*), black spot disease (*Alternaria brassicicola*), gray mold disease (*Botrytis cinerea*), and the like.

Common bean: sclerotinia rot disease (*Sclerotinia sclerotiorum*), gray mold disease (*Botrytis cinerea*), anthracnose (*Colletotrichum lindemuthianum*), angular spot disease (*Phaeoisariopsis griseola*), and the like.

Apple: powdery mildew disease (*Podosphaera leucotricha*), scab disease (*Venturia inaequalis*), Monilinia disease (*Monilinia mali*), black spot disease (*Mycosphaerella pomi*), valla canker disease (*Valsa mali*), alternaria blotch disease (*Alternaria mali*), rust disease (*Gymnosporangium yamadae*), ring rot disease (*Botryosphaeria berengeriana*), anthracnose disease (*Glomerella cingulata, Colletotrichum acutatum*), leaf srot disease (*Diplocarpon mali*), fly speck disease (*Zygophiala jamaicensis*), Sooty blotch (*Gloeodes pomigena*), violet root rot disease (*Helicobasidium mompa*), gray mold disease (*Botrytis cinerea*), and the like.

Japanese apricot: scab disease (*Cladosporium carpophilum*), gray mold disease (*Botrytis cinerea*), brown rot disease (*Monilinia mumecola*), and the like.

Persimmon: powdery mildew disease (*Phyllactinia kakicola*), anthracnose disease (*Gloeosporium kaki*), angular leaf spot (*Cercospora kaki*), and the like.

Peach: brown rot disease (*Monilinia fructicola*), scab disease (*Cladosporium carpophilum*), phomopsis rot disease (*Phomopsis* sp.), bacterial shot hole disease (*Xanthomonas campestris* pv. *pruni*), and the like.

Almond: brown rot disease (*Monilinia taxa*), spot blotch disease (*Stigmina carpophila*), scab disease (*Cladosporium carpophilum*), red leaf spot disease (*Polystigma rubrum*), alternaria blotch disease (*Alternaria alternata*), anthracnose (*Colletotrichum gloeospoides*), and the like.

Yellow peach: brown rot disease (*Monilinia fructicola*), anthracnose disease (*Colletotrichum acutatum*), black spot disease (*Alternaria* sp.), Monilinia kusanoi disease (*Monilinia kusanoi*), and the like.

Grape: gray mold disease (*Botrytis cinerea*), powdery mildew disease (*Uncinula necator*), ripe rot disease (*Glomerella cingulata, Colletotrichum acutatum*), downy mildew disease (*Plasmopara viticola*), anthracnose disease (*Elsinoe ampelina*), brown spot disease (*Pseudocercospora vitis*), black rot disease (*Guignardia bidwellii*), white rot disease (*Coniella castaneicola*), rust disease (*Phakopsora ampelopsidis*), and the like.

Pear: scab disease (*Venturia nashicola*), rust disease (*Gymnosporangium asiaticum*), black spot disease (*Alternaria kikuchiana*), ring rot disease (*Botryosphaeria berengeriana*), powdery mildew disease (*Phyllactinia mali*), *Cytospora* canker disease (*Phomopsis fukushii*), brown spot blotch disease (*Stemphylium vesicarium*), anthracnose disease (*Glomerella cingulata*), and the like.

Tea: ring spot disease (*Pestalotiopsis longiseta, P. theae*), anthracnose disease (*Colletotrichum theae-sinensis*), Net blister blight (*Exobasidium reticulatum*), and the like.

Citrus fruits: scab disease (*Elsinoe fawcettii*), blue mold disease (*Penicillium italicum*), common green mold disease (*Penicillium digitatum*), gray mold disease (*Botrytis cinerea*), melanose disease (*Diaporthe citri*), canker disease (*Xanthomonas campestris* pv. *Citri*), powdery mildew disease (*Oidium* sp.), and the like.

Wheat: powdery mildew (Blumeria *graminis* f. sp. *tritici*), red mold disease (*Gibberella zeae*), red rust disease (*Puccinia recondita*), brown snow mold disease (*Pythium iwayamai*), pink snow mold disease (*Monographella nivalis*), eye spot disease (*Pseudocercosporella herpotrichoides*), leaf scorch disease (*Septoria tritici*), glume blotch disease (*Leptosphaeria nodorum*), typhulasnow blight disease (*Typhula incarnata*), sclerotinia snow blight disease (*Myrioclerotinia borealis*), damping-off disease (*Gaeumannomyces graminis*), ergot disease (*Claviceps purpurea*), stinking smut disease (*Tilletia caries*), loose smut disease (*Ustilago nuda*), and the like.

Barley: leaf spot disease (*Pyrenophora graminea*), net blotch disease (*Pyrenophora teres*), leaf blotch disease (*Rhynchosporium secalis*), loose smut disease (*Ustilago tritici, U. nuda*), and the like.

Rice: blast disease (*Pyricularia oryzae*), sheath blight disease (*Rhizoctonia solani*), bakanae disease (*Gibberella fujikuroi*), brown spot disease (*Cochliobolus miyabeanus*), damping-off disease (*Pythium graminicola*), bacterial leaf blight (*Xanthomonas oryzae*), bacterial seedling blight disease (*Burkholderia plantarii*), brown stripe disease (*Acidovorax avenae*), bacterial grain rot disease (*Burkholderia glumae*), *Cercospora* leaf spot disease (*Cercospora oryzae*), false smut disease (*Ustilaginoidea virens*), rice brown spot disease (*Alternaria alternata, Curvularia intermedia*), kernel discoloration of rice (*Alternaria padwickii*), pink coloring of rice grains (*Epicoccum purpurascens*), and the like.

Tobacco: sclerotinia rot disease (*Sclerotinia sclerotiorum*), powdery mildew disease (*Erysiphe cichoracearum*), phytophthora rot disease (*Phytophthora nicotianae*), and the like.

Tulip: gray mold disease (*Botrytis cinerea*), and the like.

Sunflower: downy mildew disease (*Plasmopara halstedii*), sclerotinia rot disease (*Sclerotinia sclerotiorum*), and the like.

Bent grass: *Sclerotinia* snow blight (*Sclerotinia borealis*), Large patch (*Rhizoctonia solani*), Brown patch (*Rhizoctonia solani*), Dollar spot (*Sclerotinia homoeocarpa*), blast disease (*Pyricularia* sp.), Pythium red blight disease (*Pythium aphanidermatum*), anthracnose disease (*Colletotrichum graminicola*), and the like.

Orchard grass: powdery mildew disease (*Erysiphe graminis*), and the like.

Soybean: purple stain disease (*Cercospora kikuchii*), downy mildew disease (*Peronospora manshurica*), phytophthora rot disease (*Phytophthora sojae*), rust disease (*Phakopsora pachyrhizi*), sclerotinia rot disease (*Sclerotinia sclerotiorum*), anthracnose disease (*Colletotrichum truncatum*), gray mold disease (*Botrytis cinerea*), *Sphaceloma* scab (*Elsinoe glycines*), melanoses (*Diaporthe phaseolorum* var. *sojae*), and the like.

Potato: hytophthora rot disease (*Phytophthora infestans*), early blight disease (*Alternaria solani*), scurf disease (*Thanatephorus cucumeris*), verticillium wilt disease (*Verticillium albo-atrum, V. dahlia, V. nigrescens*), and the like.

Banana: Panama disease (*Fusarium oxysporum*), Sigatoka disease (*Mycosphaerella fijiensis, M. musicola*), and the like.

Rape seed: sclerotinia rot disease (*Sclerotinia sclerotiorum*), root rot disease (*Phoma lingam*), black leaf spot disease (*Alternaria brassicae*), and the like.

Coffee: rust disease (*Hemileia vastatrix*), anthracnose (*Colletotrichum coffeanum*), leaf spot disease (*Cercospora coffeicola*), and the like.

Sugarcane: brown rust disease (*Puccinia melanocephala*), and the like.

Corn: zonate spot disease (*Gloeocercospora sorghi*), rust disease (*Puccinia sorghi*), southern rust disease (*Puccinia polysora*), smut disease (*Ustilago maydis*), brown spot disease (*Cochliobolus heterostrophus*), northern leaf blight (*Setosphaeria turcica*), and the like.

Cotton: seedling blight disease (*Pythium* sp.), rust disease (*Phakopsora gossypii*), sour rot disease (*Mycosphaerella areola*), anthracnose (*Glomerella gossypii*), and the like.

The agricultural or horticultural fungicide according to the present invention is preferably applied to plants such as: cereals; vegetables; root crops; potatoes; trees such as fruit trees, tea, coffee tree, or cocoa tree; grasses; lawn grass; or cotton.

The agricultural or horticultural fungicide according to the present invention may be applied to each part of plants, such as leaves, stems, patterns, flowers, buds, fruits, seeds, sprouts, roots, tubers, tuberous roots, shoots, or cuttings. The agricultural or horticultural fungicide according to the present invention may also be applied to improved varieties/ varieties, cultivars, as well as mutants, hybrids and genetically modified organisms (GMO) of these plants.

The agricultural or horticultural fungicide according to the present invention may be used to conduct seed treatment, foliage application, soil application, or water application, so as to control various diseases occurring in agricultural or horticultural crops, including flowers, lawns, and pastures.

The agricultural or horticultural fungicide according to the present invention may further contain other components in addition to the oxadiazole compound according to the present invention. Examples of the other components include known carriers to be used to conduct formulation. Additional examples thereof include conventionally-known fungicides, insecticidal/acaricidal agents, nematodes, soil pesticides, plant control agents, synergistic agents, fertilizers, soil conditioners, and animal feeds. The inclusion of such other components exhibits synergistic effects.

Specific examples of fungicides to be mixed with or combined with the agricultural or horticultural fungicide according to the present invention to be used are shown below.

(1) Nucleic acid biosynthesis inhibitor:

(a) RNA polymerase I inhibitor: benalaxyl, benalaxyl-M, furalaxyl, metalaxyl, metalaxyl-M, oxadixyl, clozylacon, and ofurace;

(b) adenosine deaminase inhibitor: bupirimate, dimethirimol, and ethirimol;

(c) DNA/RNA synthesis inhibitor: hymexazol, and octhilinone; and (d) DNA topoisomerase II inhibitor: oxolinic acid.

(2) Karyokinesis inhibitor and cell division inhibitor:

(a) β-tubulin polymerization inhibitor: benomyl, carbendazim, chlorfenazole, fuberidazole, thiabendazole, thiophanate, thiophanate-methyl, diethofencarb, zoxamide, and ethaboxam;

(b) cell division inhibitor: pencycuron, and (c) delocalization inhibitor of spectrin-like protein: fluopicolide.

(3) Respiration inhibitor:

(a) complex I NADH oxidation-reduction inhibitor: diflumetorim, and tolfenpyrad;

(b) complex II succinic acid dehydrogenase inhibitor: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxan, boscalid, and pyraziflumid;

(c) complex III ubiquinol oxidase Qo inhibitor: azoxystrobin, coumoxystrobin, coumethoxystrobin, enoxastrobin, flufenoxystrobin, picoxystrobin, pyraoxystrobin; pyraclostrobin, pyrametostrobin, triclopyricarb, kresoximmethyl, trifloxystrobin; dimoxystrobin, fenaminstrobin, metominostrobin, orysastrobin, famoxadone, fluoxastrobin, fenamidone, pyribencarb, and mandestrobin;

(d) complex III ubiquinol reductase Qi inhibitor: cyazofamid and amisulbrom;

(e) oxidative phosphorylation uncoupling agent: binapacryl, meptyldinocap, dinocap, fluazinam, and ferimzone;

(f) oxidative phosphorylation inhibitor (ATP synthase inhibitor): fenthin acetate, fentin chloride, and fentin hydroxide;

(g) ATP production inhibitor: silthiofam; and (h) complex III cytochrome bc1 (ubiquinone reductase) Qx (unknown) inhibitor: ametoctradin.

(4) Amino acid and protein synthesis inhibitor (a) methionine biosynthesis inhibitor: andoprim, cyprodinil, mepanipyrim, and pyrimethanil; and (b) protein synthesis inhibitor: blasticidin-S, kasugamycin, kasugamycin hydrochloride, streptomycin, and oxytetracycline.

(5) Signal transfer inhibitor:

(a) signal transfer inhibitor: quinoxyfen, and proquinazid; and (b) MAP/histidine kinase inhibitor in osmotic pressure signal transfer: fenpiconil, fludioxonil, chlozolinate, iprodione, procymidone, and vinclozolin.

(6) Lipid and Cell Membrane Synthesis Inhibitor:

(a) phospholipid biosynthesis and methyltransferase inhibitor: edifenphos, iprobenfos, pyrazophos, and isoprothiolane;

(b) lipid peroxide agent: biphenyl, chloroneb, dichloran, quintozene, tecnazene, tolclofos-methyl, and etridiazole;

(c) agents affecting cell membrane: iodocarb, propamocarb, propamocarb-hydrochloride, propamocarb-fosetylate, and prothiocarb;

(d) microorganisms disturbing pathogen cell membrane: *Bacillus subtilis, Bacillus subtilis* strain QST713, *Bacillus subtilis* strain FZB24, *Bacillus subtilis* strain MBI600, *Bacillus subtilis* strain D747, and *Bacillus amyloliquefaciens*; and (e) agents disturbing cell membrane: *Melaleuca alternifolia* (tea tree) extract.

(7) Cell membrane sterol biosynthesis inhibitor:

(a) C14 position demethylation inhibitor in sterol biosynthesis: triforine, pyrifenox, pyrisoxazole, fenarimol, flurprimidol, nuarimol, imazalil, imazalil-sulphate, oxpoconazole fumarate, pefurazoate, prochloraz, triflumizole, viniconazole, azaconazole, bitertanol, bromconazole, cyproconazole, diclobutrazol, difenoconazole, diniconazole, diniconazole-M, epoxyconazole, etaconazole, fenbuconazole, fluquinconazole, flusilazole, flutriafol, furconazole, furconazole-cis, hexaconazole, imibenconazole, ipuconazole, metconazole, myclobutanil, penconazole, propiconazole, fluquinconazole, simeconazole, tebuconazole, tetraconazole, triadimefon, triadimenol, triticonazole, prothioconazole, voriconazole and mefentrifluconazole;

(b) Δ14 reductase and Δ8→Δ7-isomerase inhibitor in sterol biosynthesis: aldimorph, dodemorph, dodemorph acetate, fenpropimorph, tridemorph, fenpropidine, piperalin and spiroxamine;

(c) 3-keto reductase inhibitor in C4 position demethylation in sterol biosynthesis system: fenhexamid and fenpyrazamine; and (d) squalene epoxidase inhibitor in sterol biosynthesis system: pyributicarb, naftifen, and terbinafine.

(8) Cell wall synthesis inhibitor (a) trehalase inhibitor: validamycin;

(b) chitin synthetase inhibitor: polyoxins, and polyoxorim; and (c) cellulose synthetase inhibitor: dimethomorph, flumorph, pyrimorph, benthiavalicarb-isopropyl, iprovalicarb, tolprocarb, valifenalate, and mandipropamide.

(9) Melanin biosynthesis inhibitor (a) reductase inhibitor in melamin biosynthesis: fthalide, pyroquilon, and tricyclazole; and (b) anhydrase inhibitor in melanin biosynthesis: carpropamid, diclocymet, and fenoxanil.

(10) Resistance-inducing agent of host plant:

(a) agents affecting salicylic acid synthetic pathway: acibenzolar-s-methyl; and (b) others: probenazole, tiadinil, isotianil, laminarin, and extract liquid of *Reynoutria sachalinensis*.

(11) Agents of which the activity is unknown: cymoxanil, fosetyl-aluminium, phosphoric acid (phosphate), tecloftalam, triazoxide, flusulfamide, diclomezine, methasulfocarb, cyflufenamid, metrafenone, pyriofenone, dodine, dodine free base, and flutianil.

(12) Agent having multy activities: copper (copper salt), bordeaux mixture, copper hydroxide, copper naphthalate, copper oxide, copper oxychloride, copper sulfate, sulfur, sulfur product, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon, chinomethionat, and fluoroimide.

(13) Other agents: DBEDC, fluorofolpet, guazatine acetate, bis (8-quinolinolato) copper (II), propamidine, chloropicrin, cyprofuram, agrobacterium, bethoxazin, diphenylamine, methyl isothiocyanate (MITC), mildiomycin, capsaicin, cufraneb, cyprosulfamide, dazomet, debacarb, dichlorophen, flumetover, fosetyl-calcium, fosetyl-sodium, irumamycin, natamycin, nitrothal isopropyl, oxamocarb, pyrrolnitrin, tebufloquin, tolnifanide, zarilamide, algophase, amicarthiazol, oxathiapiprolin, metiram zinc, benthiazole, trichlamide, uniconazole, oxyfenthiin, picarbutrazox, fenpicoxamid, dichlobentiazox, quinofumelin, thiuram, ambam, *Agrobacterium radiobacter, Coniothyrium minitans, Pseudomonas fluorescens, Pseudomonas rhodesiae, Talaromyces flavus, Trichodenna atroviride, Erwinia carotovora* subsp. *carotovora, Bacillus simplex, variovorax paradoxus*, and *Lactobacillus plantarum*.

Specific examples of insecticides, acaricides, nematocides, soil pesticides, and anthelmintics, which may be mixed or used together with the agricultural or horticultural fungicide according to the present invention are shown below.

(1) Acetylcholine esterase inhibitor:

(a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, cloethocarb, metam-sodium, and promecarb;

(b) Organic phosphorus-based: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion, bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, jodfenphos, methacrifos, pirimiphos-ethyl, phosphocarb, propaphos, prothoate, and sulprofos.

(2) GABA-agonistic chloride ion channel antagonist: acetoprole, chlordane, endosulfan, ethiprole, fipronil, pyrafluprole, pyriprole, camphechlor, heptachlor, and dienochlor.

(3) Sodium channel modulator: acrinathrin, d-cis-trans allethrin, d-trans allethrin, bifenthrin, bioallethrin, bioallethrin s-cyclopentyl isomer, bioresmethrin, cycloprothrin, cyfluthrin, β-cyfluthrin, cyhalothrin, λ-cyhalothrin, γ-cyhalothrin, cypermethrin, α-cypermethrin, β-cypei inethrin, θ-cypettliethrin, ζ-cypermethrin, cyphenothrin [(1R)-trans isomer], deltamethrin, (empenthrin [(EZ)-(1R)-isomer]), esfenvalerate, etofenprox, fenpropathrin, fenvalerate, flucythrinate, flumethrin, τ-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin, allethrin, pyrethrins, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, and terallethrin.

(4) Nicotinic acetylcholine receptor agonist: acetamiprid, clothianidin, dinotefuran, imidacloprid, nitenpyram, nithiazine, thiacloprid, thiamethoxam, sulfoxaflor, nicotine, flupyradifurone, and flupyrimine (5) Nicotinic acetylcholine receptor allosteric modulator: spinetoram, and spinosad.

(6) Chloride channel activator: abamectin, emamectin-benzoate, lepimectin, milbemectin, ivermectin, selamectin, doramectin, eprinomectin, moxidectin, milbemycin, milbemycin oxime, and nemadectin.

(7) Juvenile hormone-like substances: hydroprene, kinoprene, methoprene, fenoxycarb, pyriproxyfen, diofenolan, epofenonane, and triprene.

(8) Other nonspecific inhibitor: methyl bromide, chloropicrin, sulfuryl fluoride, borax, and tartar emetic.

(9) Homoptera selective feeding inhibitor: flonicamid, pymetrozine, and pyrifluquinazon.

(10) Acari growth inhibitor: clofentezine, diflovidazin, hexythiazox, and etoxazole.

(11) Microorganism-derived insect midgut inner membrane distrupting agent: *Bacillus thuringiensis* subsp. Israelensi, *Bacillus sphaericus*, *Bacillus thuringiensis* subsp. Aizawai, *Bacillus thuringiensis* subsp. Kurstaki, *Bacillus thuringiensis* subsp. *Tenebrionis*, Bt crop protein, Cry1Ab, Cry1Ac, Cry1Fa, Cry1A.105, Cry2Ab, Vip3A, mCry3A, Cry3Ab, Cry3Bb, and Cry34Ab1/Cry35Ab1.

(12) Mitochondria ATP biosynthesis enzyme inhibitor: diafenthiuron, azocyclotin, cyhexatin, fenbutatin oxide, propargite, and tetradifon.

(13) Oxidative phosphorylation uncoupling agent: chlorfenapyr, sulfluramid, DNOC; binapacryl, dinobuton, and dinocap.

(14) Nicotinic acetylcholine receptor channel blocker: bensultap, cartap hydrochloride, nereistoxin, thiosultap-sodium, and thiocyclam.

(15) Chitin synthesis inhibitor: bistrifluron, chlorfluazuron, diflubenzuron, flucycloxuron, flufenoxuron, hexaflumuron, lufenuron, novaluron, noviflumuron, teflubenzuron, triflumuron, buprofezin, and fluazuron.

(16) Diptera molting disturbing agent: cyromazine

(17) Molting hormone receptor agonist: chromafenozide, halofenozide, methoxyfenozide, and tebufenozide.

(18) Octopamine receptor agonist: amitraz, demiditraz, and chlordimefoun.

(19) Mitochondria electron transfer chain complex III inhibitor: acequinocyl, fluacrypyrim, and hydramethylnon.

(20) Mitochondria electron transfer chain complex I inhibitor: fenazaquin, fenpyroximate, pyrimidifen, pyridaben, tebufenpyrad, tolfenpyrad, and rotenone.

(21) Voltage-dependent sodium channel blocker: indoxacarb, and metaflumizone.

(22) Acetyl CoA carboxylase inhibitor: spirodiclofen, spiromesifen, and spirotetramat.

(23) Mitochondria electron transfer chain complex IV inhibitor: aluminium phosphide, calcium phosphide, phosphine, zinc phosphide, and cyanide.

(24) Mitochondria electron transfer chain complex II inhibitor: cyenopyrafen, cyflumetofen, and pyflubumide.

(25) Ryanodine receptor modulator: chlorantraniliprole, cyantraniliprole, flubendiamide, cyclaniliprole, tetraniliprole.

(26) Mixed function oxidase inhibitor compound: piperonyl butoxide.

(27) Latrophilin receptor agonist: depsipeptide, cyclodepsipeptide, 24 membered cyclodepsipeptide, and emodepside.

(28) Others (action mechanism is unknown): azadirachtin, benzoximate, bifenazate, bromopropylate, quinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimine, fluphenazine, gossyplure, japonilure, metoxadiazone, oil, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazole-3-yl]-2-(1H-1,2,4-triazole-1-yl)

benzonitrile (CAS:943137-49-3), broflanilide, other metadiamides, *Steinemema carpocapsae, Steinemema glaseri, Pasteuria penetrans, Paecilomyces tenuipes, Paecilomyces fumosoroseus, Beauveria bassiana, Beauveria brongniartii, Metarhizium anisopliae*, and *Verticillium lecanii*.

(29) Anthelmintic:

(a) benzimidazole-based: fenbendazole, albendazole, triclabendazole, oxibendazole, mebendazole, oxfendazole, parbendazole, flubendazole, febantel, netobimin, thiophanate, thiabendazole, and cambendazole;

(b) salicylanilide-based: closantel, oxyclozanide, rafoxanide, and niclosamide;

(c) substituted phenol-based: nitroxinil, and nitroscanate;

(d) pyrimidine-based: pyrantel, and morantel;

(e) imidazo thiazole-based: levamisole, and tetramisole;

(f) tetrahydropyrimidine-based: praziquantel, and epsiprantel;

(g) other anthelmintic: cyclodiene, ryania, clorsulon, metronidazole, demiditraz, piperazine, diethylcarbamazine, dichlorophen, monepantel, tribendimidine, amidantel, thiacetarsamide, melarsomine, and arsenamide.

Specific examples of plant control agents, which may be mixed or used together with the pest control agent according to the present invention, are shown below.

Abscisic acid, kinetin, benzylaminopurine, 1,3-diphenylurea, forchlorfenuron, thidiazuron, chlorfenuron, dihydrozeatin, gibberellin A, gibberellin A4, gibberellin A7, gibberellin A3, 1-methylcyclopropane, N-acetyl aminoethoxyvinyl glycine (another name: aviglycine), aminooxyacetate, silver nitrate, cobalt chloride, IAA, 4-CPA, cloprop, 2,4-D, MCPB, indole-3-butyrate, dichlorprop, phenothiol, 1-naphthyl acetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl)aminobutyric acid, ethephon, chlormequat, mepiquat chloride, benzyladenine, 5-amino levulinic acid, and daminozide.

{Preparation Formulation}

The agricultural or horticultural fungicide according to the present invention is not particularly limited by the dosage form thereof. Examples of the dosage form include wettable powders, emulsions, powders, granules, water-soluble agents, suspensions, granular wettable powders, and tablets. The method for preparing formulation is not particularly limited, and conventionally-known method may be adopted depending on the dosage form.

Several formulation examples are shown below. The preparation formulations shown below are merely examples, and may be modified within a range not contrary to the essence of the present invention, and the present invention is not limited by the following formulation examples. "Part" means "part by mass" unless otherwise specified.

Formulation Example 1: Wettable Powders 40 parts of an oxadiazole compound according to the present invention, 53 parts of diatomaceous earth, 4 parts of higher alcohol sulfuric acid ester, and 3 parts of alkyl naphthalene sulfonate were mixed uniformly, and then finely pulverized to obtain wettable powders containing 40 parts by mass of the active ingredient.

Formulation Example 2: Emulsion 30 parts of an oxadiazole compound according to the present invention, 33 parts of xylene, 30 parts of dimethylformamide, and 7 parts of polyoxyethylene alkyl allyl ether were mixed and dissolved to obtain an emulsion containing 30% by mass of the active ingredient.

Formulation Example 3: Granules 5 parts of an oxadiazole compound according to the present invention, 40 parts of talc, 38 parts of clay, 10 parts of bentonite, and 7 parts of sodium alkyl sulfate were mixed uniformly, and then finely pulverized, followed by conducting granulation to make the particle diameter thereof be 0.5 to 1.0 mm, and thus granules containing 5% by mass of the active ingredient were obtained.

Formulation Example 4: Granules 5 parts of an oxadiazole compound according to the present invention, 73 parts of clay, 20 parts of bentonite, 1 part of sodium dioctyl sulfosuccinate, and 1 part of potassium phosphate were mixed and then pulverized, followed by adding water thereto, and then kneading the mixture. Then, granulation was conducted, and the resultant was dried to obtain granules containing 5% by mass of the active ingredient.

Formulation Example 5: Suspension 10 parts of an oxadiazole compound according to the present invention, 4 parts of polyoxyethylene alkyl allyl ether, 2 parts of sodium polycarboxylate, 10 parts of glycerin, 0.2 parts of xanthan gum, and 73.8 parts of water were mixed, and then wet pulverized until the particle size became 3 microns or less to obtain a suspension containing 10% by mass of the active ingredient.

Formulation Example 6: Granular Wettable Powders 40 parts of an oxadiazole compound according to the present invention, 36 parts of clay, 10 parts of potassium chloride, 1 part of sodium alkylbenzene sulfonate, 8 parts of sodium lignin sulfonate, and 5 parts of formaldehyde condensate of sodium alkylbenzene sulfonate were mixed uniformly, and then finely pulverized. Then, an appropriate amount of water is added to the resultant, and then kneaded to a clay-like material. The clay-like material is granulated, and then dried to obtain granular wettable powders containing 40% by mass of the active ingredient.

Next, the present invention will be further specifically explained by showing examples. The present invention is not limited by the following examples.

Example 1

Synthesis of 1-(4-(5-(trifluoromethyl)-1,2,4-oxadiazol-3-yl)benzyl)pyridin-2(1H)-one

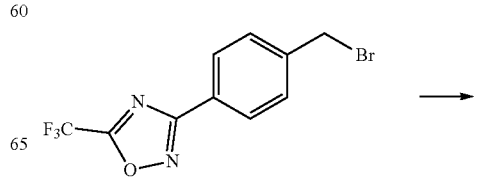

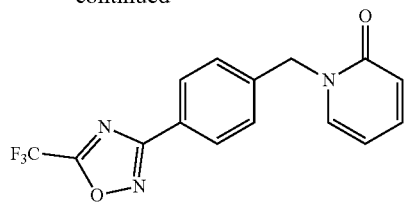

2-hydroxy pyridine (0.19 g) was dissolved in N,N-dimethylformamide (10 ml). 60% by mass of sodium hydride (0.08 g) was added to the mixture while conducting ice-cooling, and then the mixture was stirred for 1 hour at room temperature. The resultant was ice-cooled again, and then 3-(4-(bromomethyl)phenyl)-5-(trifluoromethyl)-1,2,4-oxadiazole (0.5 g) was added thereto, followed by stirring the mixture at room temperature overnight. The resultant liquid was poured into ice water, and then extracted with ethyl acetate. The extracted phase was washed with water and then washed with saturated saline. Thereafter, the resultant was dried over anhydrous magnesium sulfate. The solvent was distilled off under reduced pressure, and the resultant residue was purified by silica gel column chromatography (developing solvent: n-hexane/ethyl acetate) to obtain 0.29 g of the target compound (at a yield of 55%).

The resultant $^1$H-NMR of the target compound is shown below.

$^1$H-NMR (CDCl$_3$, δ ppm): 5.21 (s, 2H), 6.19 (t, 1H), 6.63 (d, 1H), 7.25-7.38 (m, 2H), 7.42 (d, 2H), 8.08 (d, 2H).

Example 2

Synthesis of (4-(methoxyimino)piperidin-1-yl) (4-(5-(trifluoromethyl)-1,2,4-oxadiazol-3-yl)phenyl) methanone (Step 1) 4-(5-(trifluoromethyl)-1,2,4-oxadiazol-3-yl) benzoic acid→(4-(methoxyimino)piperidin-1-yl)(4-(5-(trifluoromethyl)-1,2,4-oxadiazol-3-yl)phenyl) methanone

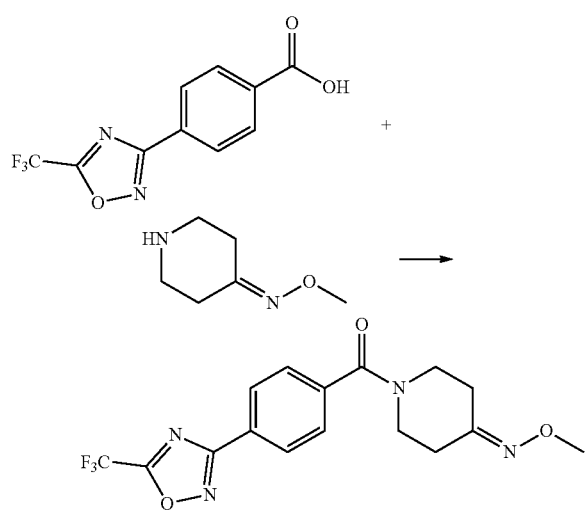

4-(5-(trifluoromethyl)-1,2,4-oxadiazol-3-yl)benzoic acid (0.24 g) was suspended in dichloromethane (10 ml). 4-(methoxyimino)piperidine (0.12 g), 4-(N,N-dimethylamino)pyridine (0.15 g) and 1-[3-(diethylamino)propyl]-3-ethylcarbodiimide hydrochloride (0.23 g) were added to the resultant, and then stirred at room temperature overnight. The resultant liquid was poured into ice water, and then extracted with chloroform, followed by conducting washing with water and then washing with saturated saline. Thereafter, the resultant was dried over anhydrous magnesium sulfate. Then, the solvent was distilled off under reduced pressure. The resultant residue was purified by silica gel column chromatography (developing solvent: n-hexane/ethyl acetate) to obtain 0.11 g of the target compound (at a yield of 32%).

The resultant $^1$H-NMR of the target compound is shown below.

$^1$H-NMR (CDCl$_3$, δ ppm): 2.27-2.76 (4H, m), 3.41-3.92 (7H, m), 7.57 (2H, d), 8.18 (2H, d).

Example 3

Synthesis of 1-(3-(ethoxyimino)azetidin-1-yl)-2-(4-(5-(trifluoromethyl)-1,2,4-oxadiazol-3-yl)phenyl) ethan-1-one (Step 1) 2-(4-(5-(trifluoromethyl)-1,2,4-oxadiazol-3-yl)phenyl)acetic acid→1-(3-(ethoxyimino)azetidin-1-yl)-2-(4-(5-(trifluoromethyl)-1,2,4-oxadiazol-3-yl) phenyl) ethan-1-one

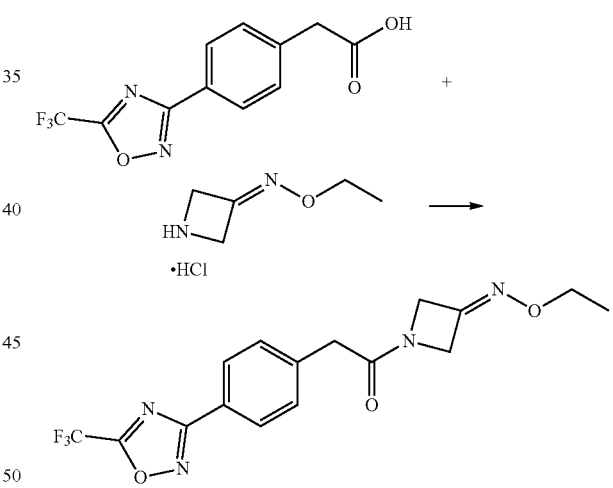

0.8 g of 2-(4-(5-(trifluoromethyl)-1,2,4-oxadiazol-3-yl) phenyl)acetic acid was suspended in 6 ml of N,N-dimethylformamide. 0.4 g of 3-(ethoxyimino)azetidine hydrochloride was added to the resultant, and then 1.5 ml of diisopropylethylamine and 2.2 g of 1-[bis(dimethylamino) methylene]-1H-1,2,3-triazolo[4,5-b]pyridinium 3-oxide hexafluorophosphate were added to the mixture while conducting ice-cooling, and then the mixture was stirred at room temperature overnight. The resultant liquid was poured into ice water, and then extracted with ethyl acetate, followed by conducting washing with water, and then washing with saturated saline. Thereafter, the resultant was dried over anhydrous magnesium sulfate. Then, the solvent was distilled off under reduced pressure. The resultant residue was purified by silica gel column chromatography (developing solvent: n-hexane/ethyl acetate) to obtain 0.28 g of the target compound (at a yield of 26%).

The resultant of the target compound is shown below.

¹H-NMR (CDCl₃, δ ppm) 1.24 (3H, t), 3.63 (2H, s), 4.11 (2H, q), 4.67-4.79 (4H, m), 7.62 (2H, d), 8.08 (2H, d).

Compounds according to the present invention prepared in the same manner as the above-mentioned examples are partially shown in Tables 1 to 18. The configuration of a nitrogen carbon double bond indicated by the wave line showing the bond between nitrogen and oxygen of an oxime group (N—O undefined stero bond) was described in the "configuration" column. "E" indicates the E configuration, "Z" indicates the Z configuration, and "E/Z" indicates that the compound is a mixture of compounds of both configurations. Tables 15 to 18 show substituents in compounds of formula (II-1). In the tables, the properties, melting point (m.p.) or refractive index (nD) of each compound are shown together as physical properties of each compound. In the tables 15 to 18, nPr denotes nomial propyl group, iPr denotes isopropyl group, Ac denotes acetyl group, Boc denotes tertiary-butoxycarbonyl group, Ph denotes phenyl group, Bn denotes benzyl group, and Bz denotes benzoyl group.

TABLE 1

| No | Formula | Configuration | Physical properties |
|----|---------|---------------|---------------------|
| 1 | | | amorphous |
| 2 | | | m.p: 162-165 (° C.) |
| 3 | | E or Z | viscous oil |
| 4 | | E or Z | viscous oil |
| 5 | | | m.p: 130-134 (° C.) |
| 6 | | | m.p: 86-88 (° C.) |

TABLE 1-continued
| No | Formula | Configuration | Physical properties |
|----|---------|---------------|---------------------|
| 7 | 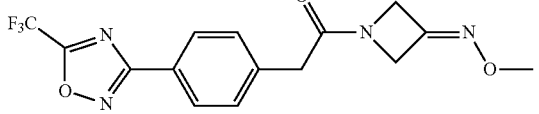 | | mp: 172-176 (° C.) |
| 8 | 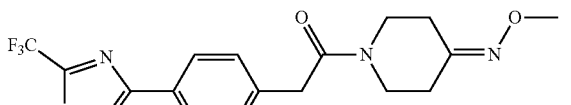 | | m.p.: 73-76 (° C.) |
| 9 | 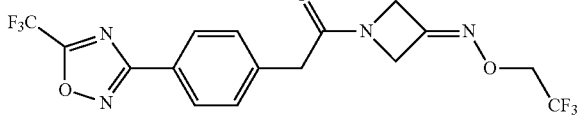 | | m.p: 126-129 (° C.) |
TABLE 2
| No. | Formula | Configuration | Physical properties |
|-----|---------|---------------|---------------------|
| 10 | 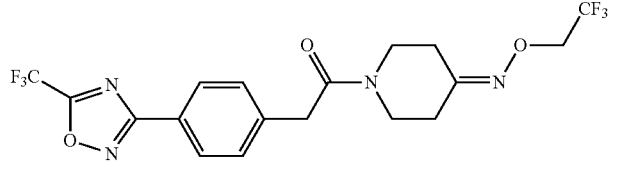 [SMILES: O=C(Cc1ccc(-c2noc(C(F)(F)F)n2)cc1)N1CCC(=NOCC(F)(F)F)CC1] | | m.p.: 84-86 (° C.) |
| 11 | 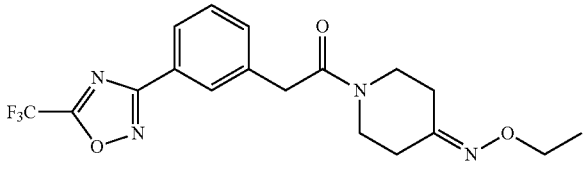 [SMILES: CCON=C1CCN(C(=O)Cc2cccc(-c3noc(C(F)(F)F)n3)c2)CC1] | | m.p.: 83-86 (° C.) |
| 12 | 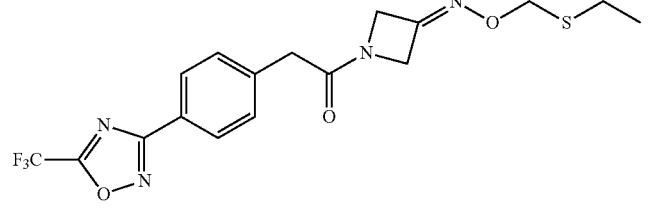 | | m.p.: 73-75 (° C.) |
| 13 | 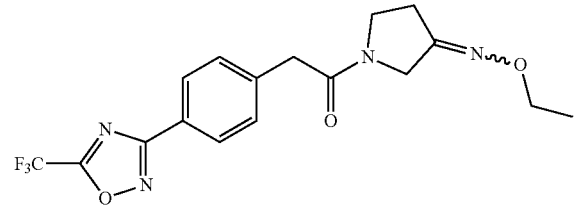 [SMILES: CCON=C1CCN(C(=O)Cc2ccc(-c3noc(C(F)(F)F)n3)cc2)C1] | E/Z | viscous oil |

TABLE 2-continued

| No. | Formula | Configuration | Physical properties |
|---|---|---|---|
| 14 | | E/Z | viscous oil |
| 15 | | | m.p.: 104-106 (° C.) |
| 16 | | | m.p.: 82-83 (° C.) |
| 17 | | | m.p.: 139-140 (° C.) |

TABLE 3

| No. | Formula | Configuration | Physical properties |
|---|---|---|---|
| 18 | | | amorphous |

TABLE 3-continued

| No. | Formula | Configuration | Physical properties |
|---|---|---|---|
| 19 | [structure with 3-(trifluoromethyl)-1,2,4-oxadiazole, phenyl, CH₂C(O)-azetidine=N-O-CH₂CH₂-OCH₃] | | m.p.: 114-116 (° C.) |
| 20 | [structure with 3-(trifluoromethyl)-1,2,4-oxadiazole, phenyl, CH₂C(O)-piperidine=N-O-CH₂-CN] | | m.p.: 126-128 (° C.) |
| 21 | [structure with 3-(trifluoromethyl)-1,2,4-oxadiazole, phenyl, CH₂C(O)-azetidine=N-O-CH₂-CN] | | m.p.: 125-126 (° C.) |
| 22 | [structure with 3-(trifluoromethyl)-1,2,4-oxadiazole, phenyl, CH₂C(O)-piperidine=N-O-iPr] | | m.p.: 96-100 (° C.) |
| 23 | [structure with 3-(trifluoromethyl)-1,2,4-oxadiazole, phenyl, CH₂C(O)-piperidine=N-O-propyl] | | amorphous |
| 24 | [structure with 3-(trifluoromethyl)-1,2,4-oxadiazole, phenyl, CH₂C(O)-piperidine=N-O-CH₂-cyclopropyl] | | amorphous |

TABLE 4

| No. | Formula | Configuration | Physical properties |
|---|---|---|---|
| 25 | (structure) | | m.p.: 191-192 (° C.) |
| 26 | (structure) | | m.p.: 71-72 (° C.) |
| 27 | (structure) | | m.p.: 68-69 (° C.) |
| 28 | (structure) | | amorphous |
| 29 | (structure) | | amorphous |
| 30 | (structure) | | m.p.: 139-141 (° C.) |

TABLE 4-continued

| No. | Formula | Configuration | Physical properties |
|-----|---------|---------------|---------------------|
| 31 | | E/Z | m.p.: 147-149 (° C.) |

TABLE 5

| No. | Formula | Configuration | Physical properties |
|-----|---------|---------------|---------------------|
| 32 | | E/Z | m.p.: 80-82 (° C.) |
| 33 | | E/Z | m.p.: 120-121 (° C.) |
| 34 | | E/Z | m.p.: 128-130 (° C.) |
| 35 | | E/Z | viscous oil |

TABLE 5-continued

| No. | Formula | Configuration | Physical properties |
|---|---|---|---|
| 36 | | | amorphous |
| 37 | | E/Z | viscous oil |
| 38 | | | viscous oil |

TABLE 6

| No. | Formula | Configuration | Physical properties |
|---|---|---|---|
| 39 | | | viscous oil |
| 40 | | | viscous oil |
| 41 | | | m.p.: 140-141 (° C.) |

TABLE 6-continued

| No. | Formula | Configuration | Physical properties |
|-----|---------|---------------|---------------------|
| 42 | | | m.p.: 90-93 (° C.) |
| 43 | | | amorphous |
| 44 | | | m.p.: 108-110 (° C.) |
| 45 | | | m.p.: 83-85 (° C.) |

TABLE 7

| No. | Formula | Configuration | Physical properties |
|-----|---------|---------------|---------------------|
| 1-1 | | | amorphous |
| 1-2 | | | m.p.: 130-133 (° C.) |

TABLE 7-continued
| No. | Formula | Configuration | Physical properties |
|---|---|---|---|
| 1-3 | 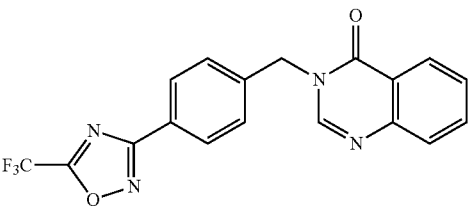 [SMILES: O=c1c2ccccc2ncn1Cc1ccc(-c2noc(C(F)(F)F)n2)cc1] | | m.p.: 178-180 (° C.) |
| 1-4 | 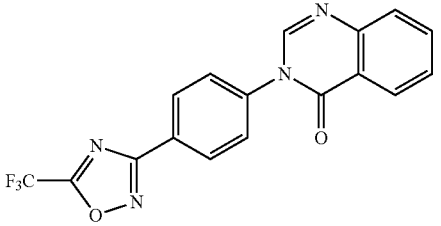 [SMILES: O=c1c2ccccc2ncn1-c1ccc(-c2noc(C(F)(F)F)n2)cc1] | | m.p.: 233-235 (° C.) |
| 1-5 | 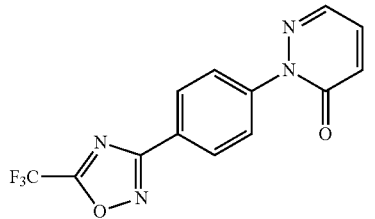 [SMILES: O=c1cccnn1-c1ccc(-c2noc(C(F)(F)F)n2)cc1] | | m.p.: 97-100 (° C.) |
| 1-6 | 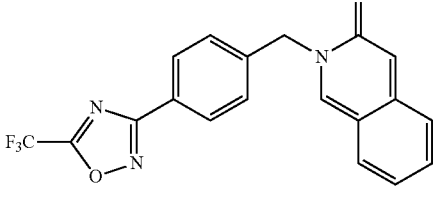 | | m.p.: 165-168 (° C.) |
| 1-7 | 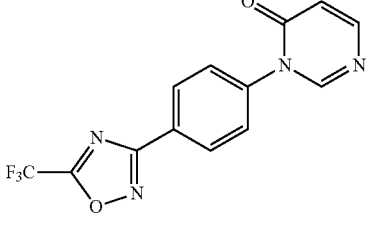 | | amorphous |
TABLE 8
| No. | Formula | Configuration | Physical properties |
|---|---|---|---|
| 1-8 | 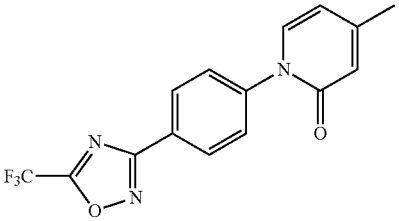 [SMILES: Cc1ccn(-c2ccc(-c3noc(C(F)(F)F)n3)cc2)c(=O)c1] | | m.p.: 151-154 (° C.) |

TABLE 8-continued
| No. | Formula | Configuration | Physical properties |
|---|---|---|---|
| 1-9 | 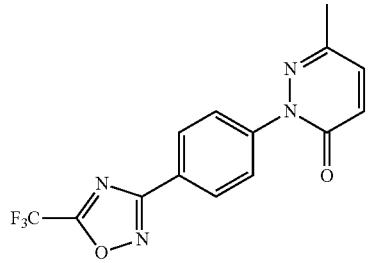 [SMILES: Cc1ccc(=O)n(-c2ccc(-c3noc(C(F)(F)F)n3)cc2)n1] | | m.p.: 78-83 (° C.) |
| 1-10 | 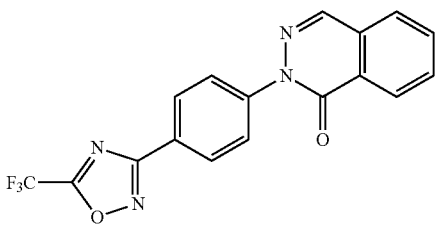 [SMILES: O=c1c2ccccc2cnn1-c1ccc(-c2noc(C(F)(F)F)n2)cc1] | | m.p.: 141-144 (° C.) |
| 1-11 | 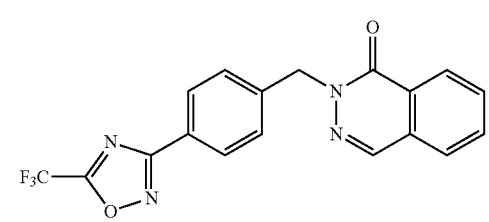 | | m.p.: 133-136 (° C.) |
| 1-12 | 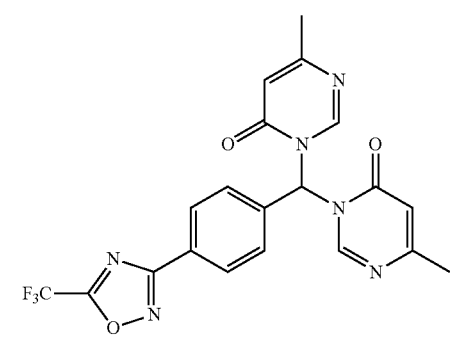 [SMILES: Cc1cc(=O)n(C(c2ccc(-c3noc(C(F)(F)F)n3)cc2)n2cnc(C)cc2=O)cn1] | | viscous oil |
| 1-13 | 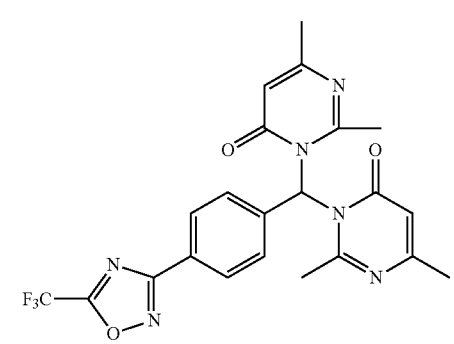 [SMILES: Cc1cc(=O)n(C(c2ccc(-c3noc(C(F)(F)F)n3)cc2)n2c(C)nc(C)cc2=O)c(C)n1] | | viscous oil |

TABLE 8-continued

| No. | Formula | Configuration | Physical properties |
|---|---|---|---|
| 1-14 | | | m.p.: 105-107 (° C.) |

TABLE 9

| No. | Formula | Configuration | Physical properties |
|---|---|---|---|
| 1-15 | | | m.p.: 122-125 (° C.) |
| 1-16 | | | m.p.: 151-153 (° C.) |
| 1-17 | | | m.p.: 145-147 (° C.) |
| 1-18 | | | m.p.: 186-188 (° C.) |

TABLE 9-continued

| No. | Formula | Configuration | Physical properties |
|---|---|---|---|
| 1-19 | | | amorphous |
| 1-20 | | | amorphous |

TABLE 10

| No. | Formula | Configuration | Physical properties |
|---|---|---|---|
| 1-21 | | | m.p.: 158-160 (° C.) |
| 1-22 | | | m.p.: 187-190 (° C.) |
| 1-23 | | | m.p.: 118-120 (° C.) |
| 1-24 | | | m.p.: 225-228 (° C.) |

TABLE 10-continued

| No. | Formula | Configuration | Physical properties |
|---|---|---|---|
| 1-25 | | | m.p.: 165-168 (° C.) |
| 1-26 | | | m.p.: 157-160 (° C.) |

TABLE 11

| No. | Formula | Configuration | Physical properties |
|---|---|---|---|
| 1-27 | | E or Z | viscous oil |
| 1-28 | | E or Z | viscous oil |
| 1-29 | | E/Z | m.p.: 82-98 (° C.) |

TABLE 11-continued

| No. | Formula | Configuration | Physical properties |
|---|---|---|---|
| 1-30 | | | m.p.: 163-166 (° C.) |
| 1-31 | | | m.p.: 94-97 (° C.) |
| 1-32 | | | m.p.: 87-89 (° C.) |
| 1-33 | | | m.p.: 74-80 (° C.) |

TABLE 12

| No. | Formula | Configuration | Physical properties |
|---|---|---|---|
| 1-34 | | | m.p.: 132-135 (° C.) |
| 1-35 | | E/Z | viscous oil |

TABLE 12-continued

| No. | Formula | Configuration | Physical properties |
|---|---|---|---|
| 1-36 | | | m.p.: 119-121 (° C.) |
| 1-37 | | E/Z | m.p.: 201-203 (° C.) |
| 1-38 | | E/Z | m.p.: 143-148 (° C.) |
| 1-39 | | | viscous oil |
| 1-40 | | E/Z | m.p.: 139-142 (° C.) |

TABLE 13

| No. | Formula | Configuration | Physical properties |
|---|---|---|---|
| 1-41 | | E/Z | m.p.: 94-96 (° C.) |

TABLE 13-continued
| No. | Formula | Configuration | Physical properties |
|---|---|---|---|
| 1-42 | | E/Z | m.p.: 103-106 (° C.) |
| 1-43 | | E/Z | amorphous |
| 1-44 | | E/Z | m.p.: 78-80 (° C.) |
| 1-45 | | E/Z | m.p.: 111-115 (° C.) |
| 1-46 | | E/Z | m.p.: 131-133 (° C.) |
TABLE 14
| No. | Formula | Configuration | Physical properties |
|---|---|---|---|
| 1-47 | | | m.p.: 192-195 (° C.) |

TABLE 14-continued
| No. | Formula | Configuration | Physical properties |
|---|---|---|---|
| 1-48 | | | viscous oil |
| 1-49 | | | viscous oil |
| 1-50 | | | viscous oil |
| 1-51 | | | viscous oil |
| 1-52 | | | m.p.: 235-237 (° C.) |
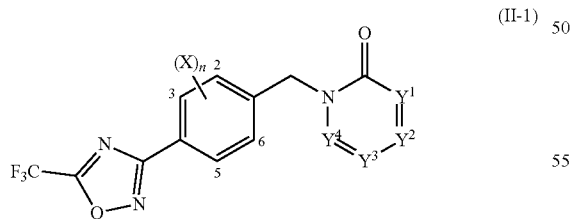
(II-1)
TABLE 15
| No. | $Y^1$ | $Y^2$ | $Y^3$ | $Y^4$ | (X) | Physical properties |
|---|---|---|---|---|---|---|
| 2-1 | CH | CH | CH | N | — | amorphous |
| 2-2 | CH | CH | C—CF$_3$ | CH | — | viscous oil |
| 2-3 | N | CH | CH | CH | — | amorphous |

TABLE 15-continued

| No. | Y¹ | Y² | Y³ | Y⁴ | (X) | Physical properties |
|---|---|---|---|---|---|---|
| 2-4 | CH | CH | N | CH | — | amorphous |
| 2-5 | C—CH₃ | CH | CH | CH | — | m.p.: 105-107(° C.) |
| 2-6 | CH | C—CH₃ | CH | CH | — | m.p.: 146-148(° C.) |
| 2-7 | CH | CH | CH | C—CH₃ | — | m.p.: 138-140(° C.) |
| 2-8 | CH | CH | C—CH₃ | CH | — | m.p.: 138-140(° C.) |
| 2-9 | CH | N | CH | CH | — | amorphous |
| 2-10 | CH | C—CF₃ | CH | CH | — | amorphous |
| 2-11 | CH | C—CN | CH | CH | — | m.p.: 187-189(° C.) |
| 2-12 | CH | C—Cl | CH | CH | — | amorphous |
| 2-13 | CH | C-(4-CF₃-phenyl) | CH | CH | — | m.p.: 142-145(° C.) |
| 2-14 | CH | C—COOCH₃ | CH | CH | — | m.p.: 148-151(° C.) |
| 2-15 | CH | C—OCH₃ | CH | CH | — | m.p.: 145-149(° C.) |
| 2-16 | CH | C—CH₃ | CH | N | — | m.p.: 86-89(° C.) |
| 2-17 | CH | C—SOCH₃ | CH | N | — | m.p.: 160-163(° C.) |
| 2-18 | CH | C—SO₂CH₃ | CH | N | — | m.p.: 192-195(° C.) |
| 2-19 | CH | C—CH₃ | N | CH | — | m.p.: 180-182(° C.) |
| 2-20 | CH | C—CH₃ | N | C—CH₃ | — | viscous oil |
| 2-21 | CH | C—SCH3 | CH | N | — | m.p.: 127-130(° C.) |
| 2-22 | CCl | C—OCH₃ | CH | N | — | m.p.: 165-169(° C.) |
| 2-23 | C—Cl | C—Cl | CH | N | — | m.p.: 158-162(° C.) |
| 2-24 | CH | C—I | CH | N | — | m.p.: 138-141(° C.) |
| 2-25 | C—CF₃ | CH | CH | CH | — | m.p.: 130-132(° C.) |

TABLE 16

| No. | Y¹ | Y² | Y³ | Y⁴ | (X) | Physical properties |
|---|---|---|---|---|---|---|
| 2-26 | CH | CH | N | C—SCH₃ | — | m.p.: 100-102(° C.) |
| 2-27 | C—CH₃ | CH | CH | N | — | m.p.: 50-53(° C.) |
| 2-28 | CH | CH | C—CH₃ | N | — | m.p.: 79-82(° C.) |
| 2-29 | CH | C—Cl | CH | N | — | m.p.: 110-113(° C.) |
| 2-30 | CH | CH | C—COOCH₂CH₃ | N | — | m.p.: 113-116(° C.) |
| 2-31 | CH | CH | C—COOCH₃ | N | — | m.p.: 140-143(° C.) |
| 2-32 | N | C—CH₃ | CH | C—CH₃ | — | viscous oil |
| 2-33 | C—COOCH₂CH₃ | CH | CH | N | — | m.p.: 114-119(° C.) |
| 2-34 | CH | C—COOCH₂CH₃ | CH | N | — | m.p.: 110-114(° C.) |
| 2-35 | CH | C—COOCH₃ | CH | N | — | m.p.: 124-127(° C.) |
| 2-36 | CH | CH | CH | N | 3-F | m.p.: 89-92(° C.) |
| 2-37 | CH | C—CH₃ | CH | N | 3-F | m.p.: 91-94(° C.) |
| 2-38 | CH | CH | CH | N | 2-F | m.p.: 70-74(° C.) |
| 2-39 | CH | C—CH₃ | CH | N | 2-F | m.p.: 87-90(° C.) |
| 2-40 | C—Cl | C—CH₃ | N | C—CH₃ | — | m.p.: 129-132(° C.) |
| 2-41 | CH | C—CH₃ | N | C—CH₃ | — | viscous oil |
| 2-42 | C—F | CH | N | C—OCH₃ | — | m.p.: 109-112(° C.) |
| 2-43 | CH | C—OCH₃ | CH | N | — | m.p.: 121-126(° C.) |
| 2-44 | C—ⁿPr | C—CH₃ | N | CH | — | m.p.: 124-126(° C.) |
| 2-45 | C—Cl | C—CH₃ | N | CH | — | m.p.: 193-195(° C.) |
| 2-46 | CH | C—F | CH | CH | — | amorphous |
| 2-47 | C-F | CH | N | CH | — | m.p.: 158-160(° C.) |
| 2-48 | C-(5-CF₃-1,2,4-oxadiazol-3-yl) | CH | CH | N | — | m.p.: 211-214(° C.) |

TABLE 17

| No. | Y¹ | Y² | Y³ | V¹ | (X) | Physical properties |
|---|---|---|---|---|---|---|
| 2-49 | CH | C—OCH₃ | N | CH | — | m.p.: 166-168(° C.) |
| 2-50 | CH | C—OCH₂CH₃ | N | CH | — | m.p.: 174-177(° C.) |
| 2-51 | CH | C—OCH₂CH₂OCH₃ | N | CH | — | m.p.: 118-120(° C.) |
| 2-52 | CH | C—OCH₂CH=CH₂ | N | CH | — | m.p.: 81-84(° C.) |
| 2-53 | C—Cl | C—OCH₂CH=CH₂ | N | CH | — | m.p.: 175-178(° C.) |
| 2-54 | C—Cl | C-NHBn | CH | N | — | m.p.: 136-139(° C.) |
| 2-55 | CH | C—OCH₂CH=CH₂ | N | N | — | m.p.: 130-133(° C.) |
| 2-56 | C—OCH₃ | CH | N | CH | — | m.p.: 170-172(° C.) |
| 2-57 | C—OH | CH | N | CH | — | m.p.: 188-190(° C.) |
| 2-58 | C—COOCH₃ | CH | N | CH | — | m.p.: 147-150(° C.) |

TABLE 17-continued

| No. | Y¹ | Y² | Y³ | V¹ (X) | Physical properties |
|---|---|---|---|---|---|
| 2-59 | C-NHBn | C—Cl | CH | N — | m.p.: 129-133(° C.) |
| 2-60 | CH | C—OCH$_2$CH$_2$SCH$_3$ | N | CH — | m.p.: 103-106(° C.) |
| 2-61 | C—OAc | CH | N | CH — | m.p.: 157-159(° C.) |
| 2-62 | C-NHBoc | CH | N | CH — | m.p.: 220-222(° C.) |
| 2-63 | C—CONH$^i$Pr | CH | N | CH — | m.p.: 216-218(° C.) |
| 2-64 | CH | C—NH$_2$ | N | CH — | m.p.: 197-200(° C.) |
| 2-65 | CH | C—NHCOCF$_3$ | N | CH — | m.p.: 172-175(° C.) |
| 2-66 | C—OCH$_2$CH$_2$OCH$_3$ | CH | N | CH — | m.p.: 112-114(° C.) |
| 2-67 | C—OCH$_2$CN | CH | N | CH — | m.p.: 179-181(° C.) |
| 2-68 | C—OCH$_2$CH$_2$CN | CH | N | CH — | m.p.: 162-164(° C.) |
| 2-69 | CH | C—NHAc | N | CH — | m.p.: 268-270(° C.) |
| 2-70 | CH | C—NAc$_2$ | N | CH — | amorphous |
| 2-71 | CH | C—NHC(=O)CH$_2$OCH$_3$ | N | CH — | m.p.: 227-230(° C.) |
| 2-72 | C—OCH$_2$C(=S)NH$_2$ | CH | N | CH — | m.p.: 200-202(° C.) |

TABLE 18

| No. | Y¹ | Y² | Y³ | Y⁴ (X) | Physical properties |
|---|---|---|---|---|---|
| 2-73 | CH | C—OCH$_2$CH$_2$OCH$_3$ | CH | N — | m.p.: 152-154(° C.) |
| 2-74 | C—Cl | C—OCH$_2$CH$_2$OCH$_3$ | CH | N — | m.p.: 135-136(° C.) |
| 2-75 | CH | C—OCH$_2$CH$_2$SOCH$_3$ | N | CH — | m.p.: 178-180(° C.) |
| 2-76 | CH | C—OCH$_2$CH$_2$SO$_2$CH$_3$ | N | CH — | m.p.: 170-173(° C.) |
| 2-77 | CH | C—NHC(=O)CH$_2$CH$_2$OCH$_3$ | N | CH — | m.p.: 258-260(° C.) |
| 2-78 | CH | C-NHBz | N | CH — | m.p.: 243-246(° C.) |
| 2-79 | CH | C-NBz$_2$ | N | CH — | m.p.: 170-172(° C.) |
| 2-80 | C—OCH$_2$CH$_2$SCH$_3$ | CH | N | CH — | viscous oil |
| 2-81 | CH | C-(1H-1,2,4-triazol-1-yl) | N | CH — | m.p.: 188-190(° C.) |
| 2-82 | C—OCH$_3$ | C—OCH$_3$ | CH | N — | m.p.: 84-85(° C.) |
| 2-83 | C—OCH$_2$CH$_2$OCH$_3$ | CH | CH | N — | m.p.: 129-130(° C.) |
| 2-84 | C—OH | C—OH | CH | N — | m.p.: 167-170(° C.) |
| 2-85 | C—NHAc | CH | N | CH — | m.p.: 256-258(° C.) |
| 2-86 | CH | C—NHPh | CH | N — | m.p.: 255-258(° C.) |
| 2-87 | CH | C—OPh | CH | N — | m.p.: 120-121(° C.) |
| 2-88 | CH | C—N(CH$_3$)$_2$ | N | CH — | m.p.: 245-247(° C.) |

Among the compounds shown in Tables 1 to 18, the compounds having viscous oil properties or amorphous properties were subjected to ¹H-NMR (CDCl$_3$) measurement. The resultant measurement values are shown in Tables 19 and 20.

TABLE 19

| No. | 1H-NMR data (δ ppm) |
|---|---|
| 1 | 2.27-2.76(4H, m), 3.41-3.92(7H, m), 7.57(2H, d), 8.18(2H, d). |
| 3 | 2.77-2.82(2H, m), 3.65-4.43(7H, m), 7.64(2H, d), 8.18(2H, d). |
| 4 | 2.70-2.82(2H, m), 3.67-4.43(7H, m), 7.64(2H, d), 8.18(2H, d). |
| 13 | 1.22-1.26(m, 3H), 1.65-1.82(m, 2H), 2.33-2.61(m, 2H), 3.47-3.83(m, 4H), 4.02-4.30(m, 2H), 7.40(d, 2H), 8.05(d, 2H). |
| 14 | 1.20-1.24(m, 3H), 1.63-1.82(m, 2H), 2.31-2.62(m, 2H), 3.47-4.50(m, 8H), 7.40(d, 2H), 8.05(d, 2H). |
| 18 | 2.22-2.65(m, 4H), 3.36-4.18(m, 13H), 7.43(d, 2H), 8.09(d, 2H). |
| 23 | 1.14(t, 3H), 1.54-175(m, 4H), 3.41-3.66(m, 8H), 3.79(s, 2H), 7.39(d, 2H), 8.06(d, 2H). |
| 24 | 0.23-0.45(m, 4H), 1.49-1.72(m, 5H), 3.39-3.82(m, 8H), 7.40(d, 2H), 8.04(d, 2H). |
| 28 | 2.22-2.58(m, 4H), 2.89-2.92(m, 3H), 3.35-3.85(m, 8H), 4.44-4.48(m, 2H), 7.43(d, 2H), 8.09. |
| 29 | 2.23-2.63(m, 7H), 2.97-3.11(m, 2H), 3.52-3.86(m, 6H), 4.37-4.52(m, 2H), 7.43(d, 2H), 8.09(d, 2H). |
| 35 | 1.21-1.29(m, 3H), 2.04-2.84(m, 5H), 3.18-3.49(m, 3H), 4.00-4.18(m, 4H), 4.53-4.99(m, 2H), 7.45(d, 2H), 8.08(d, 2H). |
| 36 | 1.20(t, 3H), 1.48(d, 3H), 3.65-3.69(m, 1H), 4.06(q, 2H), 4.39-4.82(m, 4H), 7.44(d, 2H), 8.07(d, 2H). |
| 37 | 1.17-1.63(m, 9H), 3.58-3.64(m, 1H), 3.96-4.12(m, 2H), 4.35-5.21(m, 3H), 7.45(d, 2H), 8.07(d, 2H). |
| 38 | 1.18-1.63(m, 12H), 3.58-3.64(m, 1H), 3.96-4.12(m, 2H), 4.51-5.21(m, 2H), 7.45(d, 2H), 8.07(d, 2H). |

TABLE 19-continued

| No. | 1H-NMR data (δ ppm) |
|---|---|
| 39 | 1.21-1.36(m, 6H), 3.59-3.69(m, 2H), 4.06-4.13(m, 2H), 4.67-5.03(m, 5H), 7.64(d, 2H), 8.12(d, 2H). |
| 40 | 1.21-1.28(m, 3H), 3.51(s, 3H), 4.06-4.15(m, 2H), 4.67-4.99(m, 5H), 7.62(d, 2H), 8.13(d, 2H). |
| 43 | 1.24(t, 3H), 4.12(q, 2H), 4.76-4.80(m, 2H), 5.04-5.08(m, 2H), 7.75(d, 2H), 8.21(d, 2H). |
| 1-1 | 5.21(s, 2H), 6.19(t, 1H), 6.63(d, 1H), 7.25-7.38(m, 2H), 7.43(d, 2H), 8.08(d, 2H). |
| 1-7 | 5.22(s, 2H), 6.40(d, 1H), 6.88(s, 1H), 7.33(d, 1H), 7.42(d, 2H), 8.10(d, 2H). |
| 1-12 | 2.46(s, 6H), 6.68(s, 2H), 7.84(d, 2H), 8.17(d, 2H), 8.60(s, 1H), 8.65(s, 2H). |
| 1-13 | 2.40(s, 6H), 2.47(s, 6H), 6.47(s, 2H), 7.84(d, 2H), 7.96(s, 1H), 8.17(d, 2H). |
| 1-19 | 1.80(d, 2H), 6.40(q, 1H), 6.96(d, 1H), 7.16(d, 1H), 7.55(d, 2H), 7.83(s, 1H), 8.05(d, 2H). |
| 1-20 | 1.78(d, 3H), 2.20(s, 3H), 6.36(q, 1H), 6.76(s, 1H), 7.54(d, 2H), 7.71(s, 1H), 8.04(d, 2H). |

TABLE 20

| No. | 1H-NMR data (δ ppm) |
|---|---|
| 1-27 | 3.68(s, 3H), 5.56(s, 2H), 6.88-7.11(m, 2H), 7.69-7.76(m, 3H), 8.04(d, 2H). |
| 1-28 | 3.72(s, 3H), 5.59(s, 2H), 6.89-7.12(m, 2H), 7.69-7.76(m, 3H), 8.04(d, 2H). |
| 1-35 | 5.58(s, 2H), 6.88-7.11(m, 2H), 7.69-7.76(m, 3H), 8.04(d, 2H), 8.38(s, 1H). |
| 1-39 | 1.12-1.24(m, 6H), 3.98-4.55(m, 3H), 6.88-7.11(m, 2H), 7.69-7.76(m, 3H), 8.04(d, 2H). |
| 1-43 | 4.97-5.22(m, 4H), 5.85(s, 1H), 6.99-7.47(m, 5H), 8.05-8.12(m, 3H). |
| 1-48 | 1.48(s, 9H), 2.65-2.82(m, 2H), 3.66-3.69(m, 2H), 4.36-4.42(m, 2H), 5.32-5.38(m, 2H), 7.33(d, 2H), 8.08(d, 2H). |
| 1-49 | 2.46(s, 3H), 2.65-2.72(m, 2H), 3.68-3.89(m, 2H), 4.42-4.57(m, 2H), 5.36(s, 2H), 7.33(d, 2H), 8.08(d, 2H). |
| 1-50 | 2.65-2.72(m, 2H), 3.44(s, 3H), 3.68-3.89(m, 2H), 4.19(s, 2H), 4.42-4.57(m, 2H), 5.35(s, 2H), 7.33(d, 2H), 8.08(d, 2H). |
| 1-51 | 2.65-2.72(m, 2H), 3.68-3.89(m, 2H), 4.42-4.57(m, 2H), 5.36(s, 2H), 7.25-7.47(m, 7H), 8.08(d, 2H). |
| 2-1 | 5.38(s, 2H), 6.96(d, 1H), 7.17-7.20(m, 1H), 7.55(d, 2H), 7.78-7.79(m, 2H), 8.06(d, 2H). |
| 2-2 | 5.21(s, 2H), 6.69(d, 2H), 7.44-7.49(m, 3H), 7.68(s, 1H), 8.11(d, 2H). |
| 2-3 | 5.17(s, 2H), 6.50(d, 1H), 7.46(d, 2H), 7.89(d, 1H), 8.11(d, 2H), 8.18(s, 1H). |
| 2-4 | 5.17(s, 2H), 6.31-6.34(m, 1H), 7.49(d, 2H), 7.64-7.69(m, 1H), 8.11(d, 2H), 8.61-8.63(m, 1H). |
| 2-9 | 5.14(s, 2H), 7.10(d, 1H), 7.33(s, 1H), 7.46(d, 2H), 8.11(d, 2H), 8.22(s, 1H). |
| 2-10 | 5.26(s, 2H), 6.46(d, 1H), 7.05(s, 1H), 7.45(d, 2H), 7.52(d, 1H), 8.11(d, 2H). |
| 2-12 | 5.22(s, 2H), 6.40(d, 1H), 6.88(s, 1H), 7.33(d, 1H), 7.42(d, 2H), 8.10(d, 2H). |
| 2-20 | 2.27(s, 3H), 2.42(s, 3H), 5.34(s, 2H), 6.31(s, 1H), 7.33(d, 2H), 8.08(d, 2H). |
| 2-32 | 2.29(s, 3H), 2.39(s, 3H), 5.35(s, 2H), 6.14(s, 1H), 7.35(d, 2H), 8.06(d, 2H). |
| 2-41 | 2.47(s, 3H), 5.37(s, 2H), 6.46(d, 1H), 7.33(d, 2H), 7.84(d, 2H), 8.09(d, 2H). |
| 2-46 | 5.21(s, 2H), 6.40(d, 1H), 6.88(s, 1H), 7.33(d, 1H), 7.42(d, 2H), 8.10(d, 2H). |
| 2-70 | 2.35(s, 6H), 5.16(s, 2H), 6.46(s, 1H), 7.43(d, 2H), 8.02-8.21(m, 2H). |
| 2-80 | 2.22(s, 3H), 2.92(t, 2H), 4.16(t, 2H), 5.19(s, 2H), 7.48(d, 2H), 7.90(s, 1H), 8.06-8.10(m, 3H). |

(Biological Test)

The following test examples show that the oxadiazole compound according to the present invention is useful as an active ingredient of an agricultural or horticultural fungicide.

(Preparation of Test Emulsion)

5 parts by, mass of an oxadiazole compound, 93.5 parts by mass of dimethylformamide, and 1.5 parts by mass of polyoxyethylene alkyl aryl ether were mixed and dissolved to obtain an emulsion (I) containing 5% by mass of the active ingredient.

The control value was calculated by the following formula.

Control value (%)=100−{blotch area ratio in treated area/blotch area ratio in untreated area}×100

(Test Example 1) Wheat Red Rust Disease Control Test

Water was added to the emulsion (I) such that the concentration of the oxadiazole compound became 100 ppm by mass, and then the oxadiazole compound was dissolved to obtain a pharmaceutical solution. Then, the pharmaceutical solution was sprayed on wheat young seedings (variety "Norin 61" at the first to second leaf stage) grown in nursery pots. After air-drying, the wheat young seedings sprayed with the pharmaceutical solution were inoculated with summer spores of wheat red rust pathogen (*Puccinia recondita*) by spraying the summer spores (in treated area).

As a control, wheat young seedings that were not sprayed with the pharmaceutical solution were inoculated in the same manner as mentioned above (in untreated area).

The wheat young seedings were placed under humid conditions at 20° C. for 1 day. Then, the wheat young seedings were released from humidification and placed still in the greenhouse at 20° C. After 12 days passed from inoculation, leaves of the wheat seedings were visually observed to measure the blotch area ratio, and the control value was calculated.

The compounds shown in Table 21 were subjected to the wheat red rust disease control test. The control value of all of the compounds was 75% or more.

TABLE 21

| Compound No. | | | | | |
|---|---|---|---|---|---|
| 1 | 29 | 1-13 | 1-31 | 2-4 | 2-64 |
| 2 | 36 | 1-14 | 1-47 | 2-5 | 2-65 |
| 3 | 1-1 | 1-15 | 1-48 | 2-6 | 2-75 |
| 4 | 1-2 | 1-18 | 2-1 | 2-8 | 2-77 |
| 5 | 1-10 | 1-21 | 2-2 | 2-25 | 43 |
| 28 | 1-12 | 1-24 | 2-3 | 2-26 | 2-85 |

(Test Example 2) Wheat Red Rust Disease Control Test

Water was added to the emulsion (I) such that the concentration of the oxadiazole compound became 6.3 ppm by mass to obtain a pharmaceutical solution. Then, the pharmaceutical solution was sprayed on wheat young seedings (variety "Norin 61" at the first to second leaf stage) grown in nursery pots. After air-drying, the wheat young seedings sprayed with the pharmaceutical solution were inoculated with summer spores of wheat red rust pathogen (*Puccinia recondita*) by spraying the summer spores (in treated area).

As a control, wheat young seedings that were not sprayed with the pharmaceutical solution were inoculated in the same manner as mentioned above (in untreated area).

The wheat young seedings were placed under humid conditions at 20° C. for 1 day. Then, the wheat young seedings were released from humidification and placed still in the greenhouse at 20° C. After 12 days passed from inoculation, leaves of the wheat seedings were visually observed to measure the blotch area ratio, and the control value was calculated.

The compounds shown in Table 22 were subjected to the wheat red rust disease control test. The control value of all of the compounds was 75% or more.

TABLE 22

| Compound No. | | | | | | |
|---|---|---|---|---|---|---|
| 1 | 23 | 1-20 | 2-5 | 2-27 | 2-44 | 2-58 |
| 3 | 24 | 1-23 | 2-6 | 2-28 | 2-45 | 2-66 |
| 4 | 26 | 1-26 | 2-7 | 2-33 | 2-46 | 2-67 |
| 5 | 30 | 1-30 | 2-8 | 2-36 | 2-47 | 2-68 |
| 6 | 41 | 1-31 | 2-12 | 2-37 | 2-49 | 2-72 |
| 9 | 1-1 | 1-32 | 2-15 | 2-38 | 2-50 | 2-73 |
| 10 | 1-2 | 1-33 | 2-16 | 2-39 | 2-51 | 2-76 |
| 13 | 1-8 | 1-38 | 2-19 | 2-40 | 2-54 | 31 |
| 14 | 1-9 | 1-51 | 2-20 | 2-41 | 2-55 | 39 |
| 19 | 1-15 | 2-1 | 2-22 | 2-42 | 2-56 | 40 |
| 21 | 1-19 | 2-4 | 2-26 | 2-43 | 2-57 | |

(Test Example 3) Wheat Leaf Blotch Disease Control Test

Water was added to the emulsion (I) such that the concentration of the oxadiazole compound became 100 ppm by mass to obtain a pharmaceutical solution. Then, the pharmaceutical solution was sprayed on wheat young seedings (variety "Apogee" at the first to second leaf stage) grown in nursery pots. After air-drying, the wheat young seedings sprayed with the pharmaceutical solution were inoculated with conidia of wheat leaf blotch pathogen (*Septoria tritici*) by spraying the conidia (in treated area).

As a control, wheat young seedings that were not sprayed with the pharmaceutical solution were inoculated in the same manner as mentioned above (in untreated area).

The wheat young seedings were placed under humid conditions at 20° C. for 3 days. Then, the wheat young seedings were placed under illumination for 18 days to 25 days, followed by visually observing leaves of the wheat seedings to measure the blotch area ratio, and the control value was calculated.

The compounds shown in Table 23 were subjected to the wheat leaf blotch disease control test. The control value of all of the compounds was 75% or more.

TABLE 23

| Compound No. | | | |
|---|---|---|---|
| 3 | 1-33 | 2-19 | 2-51 |
| 4 | 1-38 | 2-20 | |
| 5 | 1-47 | 2-44 | |
| 1-1 | 1-51 | 2-45 | |
| 1-2 | 2-12 | 2-49 | |

(Test Example 4) Wheat Leaf Blotch Disease Control Test

Water was added to the emulsion (I) such that the concentration of the oxadiazole compound became 6.3 ppm by mass to obtain a pharmaceutical solution. Then, the pharmaceutical solution was sprayed on wheat young seedings (variety "Apogee" at the first to second leaf stage) grown in nursery pots. After air-drying, the wheat young seedings sprayed with the pharmaceutical solution were inoculated with conidia of wheat leaf blotch pathogen (*Septoria tritici*) by spraying the conidia (in treated area).

As a control, wheat young seedings that were not sprayed with the pharmaceutical solution were inoculated in the same manner as mentioned above (in untreated area).

The wheat young seedings were placed under humid conditions at 20° C. for 3 days. Then, the wheat young seedings were placed under illumination for 18 days to 25 days, followed by visually observing leaves of the wheat seedings to measure the blotch area ratio, and the control value was calculated.

Compounds 5, 2-49 and 2-51 were subjected to the wheat leaf blotch disease control test. The control value of all of the compounds was 75% or more.

(Test Example 5) Wheat Red Rust Disease Control Test (Residual Efficacy Test)

Water was added to the emulsion (I) such that the concentration of the oxadiazole compound became 25 ppm by mass, and then the oxadiazole compound was dissolved to obtain a pharmaceutical solution. Then, the pharmaceutical solution was sprayed on wheat young seedings (variety "Norin 61" at the first to second leaf stage) grown in nursery pots and then the wheat young seedings were allowed to grow in the greenhouse at 20° C. for 7 days. After 7 days passed from spraying, the wheat young seedings sprayed with the pharmaceutical solution were inoculated with summer spores of wheat red rust pathogen (*Puccinia recondita*)

by spraying the summer spores, and then placed under humid conditions at 20° C. for 1 day. Then, the wheat young seedings were released from humidification and placed still in the greenhouse at 20° C. (in treated area).

As a control, wheat young seedlings that were not sprayed with the pharmaceutical solution were inoculated in the same manner as mentioned above, and then placed still in the greenhouse at 20° C. (in untreated area).

After 12 days passed from inoculation, leaves of the wheat seedings were visually observed to measure the blotch area ratio.

The compounds 5, 1-15, 1-21, 1-23, 2-19, 2-21, 2-22, 2-37, 2-40, 2-42, 2-43, 2-44, 2-45, 2-49 and 2-51 were subjected to the wheat red rust disease control test. The control value of all of the compounds was 75% or more.

(Test Example 6) Wheat Red Rust Disease Control Test (Residual Efficacy Test)

Water was added to the emulsion (I) such that the concentration of the oxadiazole compound became 6.3 ppm by mass, and then the oxadiazole compound was dissolved to obtain a pharmaceutical solution. Then, the pharmaceutical solution was sprayed on wheat young seedlings (variety "Norin 61" at the first to second leaf stage) grown in nursery pots and then the wheat young seedlings were allowed to grow in the greenhouse at 20° C. for 7 days. After 7 days passed from spraying, the wheat young seedlings sprayed with the pharmaceutical solution were inoculated with summer spores of wheat red rust pathogen (*Puccinia recondita*) by spraying the summer spores, and then placed under humid conditions at 20° C. for 1 day. Then, the wheat young seedings were released from humidification and placed still in the greenhouse at 20° C. (in treated area).

As a control, wheat young seedlings that were not sprayed with the pharmaceutical solution were inoculated in the same manner as mentioned above, and then placed still in the greenhouse at 20° C. (in untreated area).

After 12 days passed from inoculation, leaves of the wheat seedings were visually observed to measure the blotch area ratio.

The compounds 5, 1-23, 2-21, 2-22, 2-40, 2-44, 2-45, 2-49 and 2-51 were subjected to the wheat red rust disease control test. The control value of all of the compounds was 75% or more.

Since the compounds randomly selected from the oxadiazole compounds according to the present invention exhibited the above-described effects, it is understood that the oxadiazole compound according to the present invention, involving aspects of compounds that are not mentioned above, is a compound that exhibits fungicidal activities without causing harmful effects on plants and that provides less toxicity on human, animal, or fish, and less effects on environment.

INDUSTRIAL APPLICABILITY

The oxadiazole compound according to the present invention has an excellent fungicidal activity and an excellent safety, and can be synthesized industrially advantageously. The agricultural or horticultural fungicide according to the present invention exhibits an excellent control effect without causing harmful effects on plants and provides less toxicity on human, animal, or fish, and less effects on environment.

The invention claimed is:
1. A compound of formula (I) or a salt thereof:

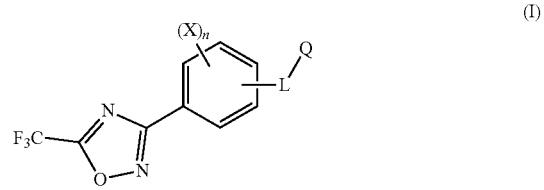

(I)

wherein, in the formula (I),
X represents a substituted or unsubstituted C1-6 alkyl group, a substituted or unsubstituted C1-6 alkoxy group or a halogeno group,
n represents a chemically acceptable number of X, and is an integer of 0 to 4, and, when n is 2 or more, X is identical to or different from each other,
L represents a single bond, or a substituted or unsubstituted C1-6 alkylene group,
Q represents a group of formula (Q-1) or formula (Q-2):

(Q-1)

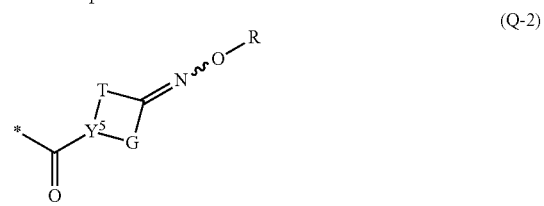

(Q-2)

in the formula (Q-1) and the formula (Q-2), * represents a bonding position,
in the formula (Q-1),
$Y^1$ represents a nitrogen atom or $CR^1$,
$Y^2$ represents a nitrogen atom or $CR^2$,
$Y^3$ represents a nitrogen atom or $CR^3$,
$Y^4$ represents a nitrogen atom or $CR^4$,
provided that, at least two of $Y^1$ to $Y^4$ do not represent nitrogen atoms,
$R^1$, $R^2$, $R^3$, and $R^4$ each independently represent a hydrogen atom, a substituted or unsubstituted C1-6 alkyl group, a hydroxyl group, a substituted or unsubstituted C1-6 alkoxy group, a substituted or unsubstituted C1-6 alkoxycarbonyl group, a substituted or unsubstituted C1-6 alkylcarbonyloxy group, a substituted or unsubstituted C1-6 alkylthio group, a substituted or unsubstituted alkylsulfinyl group, a substituted or unsubstituted alkylsulfonyl group, a substituted or unsubstituted C6-10 aryl group, a substituted or unsubstituted 5- to 6-membered heterocyclyl group, a substituted or unsubstituted C6-10 aryloxy group, a substituted or unsubstituted amino group, a substituted or unsubstituted aminocarbonyl group, a halogeno group or a cyano group,
at least one of $R^1$, $R^2$, $R^3$, and $R^4$ represents a substituted C1-6 alkoxy group, and a substituent on the substituted C1-6 alkoxy group is a halogeno group, a C2-6 alkenyl group, a C1-6 alkoxy group, a C1-6 alkylthio group, a C1-6 alkylsulfinyl group, a C1-6 alkylsulfonyl group, a substituted or unsubstituted C1-6 alkoxyimino group, a 5- to 6-membered saturated heterocyclyloxyimino group, a C6-10 aryloxyimino group, a cyano group or an aminothiocarbonyl group, in the formula (Q-2), R represents a hydrogen atom, a 5- to 6-membered saturated heterocyclyl group or a substituted or unsubstituted C1-6 alkyl group, G represents a substituted or unsubstituted C1-6 alkylene group, T represents a substituted or unsubstituted C1-6 alkylene group, and $Y^5$ represents a nitrogen atom or CH.

2. The compound or the salt thereof according to claim 1, wherein the formula (I) is formula (II):

(II)

in the formula (II), X, n and L represent the same groups as those in the formula (I), and $Y^1$ to $Y^4$ represent the same groups as those in the formula (Q-1).

3. The compound or the salt thereof according to claim 1, wherein the formula (I) is formula (III):

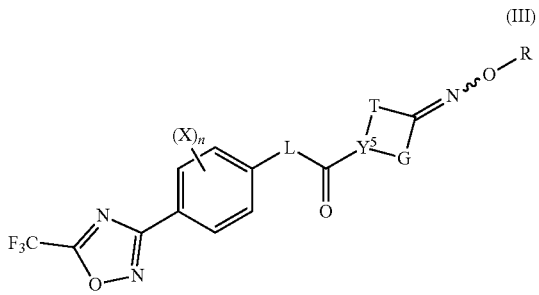

(III)

in the formula (III), X, n and L represent the same groups as those in the formula (I), and R, G, T and $Y^5$ represent the same groups as those in the formula (Q-2).

4. An agricultural or horticultural fungicide comprising, as an active ingredient thereof, at least one selected from the group consisting of a compound and a salt thereof of claim 1.

* * * * *